(12) United States Patent
Tomioka

(10) Patent No.: US 10,089,754 B2
(45) Date of Patent: *Oct. 2, 2018

(54) UNEVENNESS INSPECTION SYSTEM, UNEVENNESS INSPECTION METHOD, AND UNEVENNESS INSPECTION PROGRAM

(71) Applicant: SATURN LICENSING LLC, New York, NY (US)

(72) Inventor: Satoshi Tomioka, Kanagawa (JP)

(73) Assignee: Saturn Licensing LLC, New York, NY (US)

( * ) Notice: Subject to any disclaimer, the term of this patent is extended or adjusted under 35 U.S.C. 154(b) by 227 days.

This patent is subject to a terminal disclaimer.

(21) Appl. No.: 14/769,384

(22) PCT Filed: Feb. 18, 2014

(86) PCT No.: PCT/JP2014/053706
§ 371 (c)(1),
(2) Date: Aug. 20, 2015

(87) PCT Pub. No.: WO2014/136561
PCT Pub. Date: Sep. 12, 2014

(65) Prior Publication Data
US 2016/0011121 A1    Jan. 14, 2016

(30) Foreign Application Priority Data
Mar. 4, 2013    (JP) ................................. 2013-041573

(51) Int. Cl.
*G06T 7/90* (2017.01)
*G06T 7/00* (2017.01)
(Continued)

(52) U.S. Cl.
CPC ................ *G06T 7/90* (2017.01); *G01J 3/506* (2013.01); *G01N 21/8851* (2013.01);
(Continued)

(58) Field of Classification Search
None
See application file for complete search history.

(56) References Cited

U.S. PATENT DOCUMENTS

| 4,963,828 A | 10/1990 | Kawame |
| 9,534,957 B2 * | 1/2017 | Nagamine ............... G01J 3/462 |

(Continued)

FOREIGN PATENT DOCUMENTS

| CN | 1996441 A | 7/2007 |
| CN | 102054175 A | 5/2011 |

(Continued)

OTHER PUBLICATIONS

Extended European Search Report dated Dec. 8, 2016 in patent application No. 14759671.2.

(Continued)

*Primary Examiner* — David N Werner
(74) *Attorney, Agent, or Firm* — Oblon, McClelland, Maier & Neustadt, L.L.P.

(57) ABSTRACT

An unevenness inspection system includes an image pickup section configured to acquire a picked-up image of an inspection target, an image generation section configured to generate a color-unevenness inspection image and a luminance-unevenness inspection image, based on the picked-up image, a calculation section configured to use both of the color-unevenness inspection image and the luminance-unevenness inspection image to calculate an evaluation parameter, and an inspection section configured to use the calculated evaluation parameter to perform unevenness inspection. The image generation section generates the color-unevenness inspection image and the luminance-unevenness inspection image, based on a filter-processed color-component image and a filter-processed luminance-component image. The calculation section calculates the (Continued)

evaluation parameter in consideration of unevenness visibility with respect to both of color and luminance.

21 Claims, 17 Drawing Sheets

(51) Int. Cl.
    *G06T 7/44*     (2017.01)
    *G01J 3/50*     (2006.01)
    *H04N 17/04*     (2006.01)
    *G01N 21/88*     (2006.01)
    *H04N 9/07*     (2006.01)
    *G02F 1/13*     (2006.01)

(52) U.S. Cl.
CPC .......... *G06T 7/0002* (2013.01); *G06T 7/0004* (2013.01); *G06T 7/44* (2017.01); *H04N 9/07* (2013.01); *H04N 17/04* (2013.01); *G01N 2201/062* (2013.01); *G02F 1/1309* (2013.01); *G06T 2207/10024* (2013.01); *G06T 2207/30121* (2013.01); *G09G 2320/0233* (2013.01); *G09G 2320/0242* (2013.01); *G09G 2320/0693* (2013.01)

(56) References Cited

U.S. PATENT DOCUMENTS

| | | | | |
|---|---|---|---|---|
| 2002/0176623 A1* | 11/2002 | Steinberg | ........... | G06K 9/00228 382/165 |
| 2005/0196037 A1* | 9/2005 | Muenzenmayer | ... | G06K 9/3233 382/159 |
| 2012/0327399 A1* | 12/2012 | Nagamine | ............... | G01J 3/462 356/73 |
| 2017/0074724 A1* | 3/2017 | Nagamine | ............... | G01J 3/462 |

FOREIGN PATENT DOCUMENTS

| | | |
|---|---|---|
| CN | 102842276 A | 12/2012 |
| EP | 2 326 103 A1 | 5/2011 |
| EP | 2 966 430 A1 | 1/2016 |
| JP | 1-225296 A | 9/1989 |
| JP | 10-002800 A | 1/1998 |
| JP | 10-096681 A | 4/1998 |
| JP | 11-215523 A | 8/1999 |
| JP | 2001-28059 A | 1/2001 |
| JP | 2003-057146 A | 2/2003 |
| JP | 2006-119073 A | 5/2006 |
| JP | 2007-198850 A | 9/2007 |
| JP | 2013-029491 A | 7/2013 |
| KR | 10-2007-0071277 A | 7/2007 |
| TW | I265727 B | 11/2006 |

OTHER PUBLICATIONS

Andrew B. Watson, "31.1: Invited Paper: The Spatial Standard Observer: A Human Vision Model for Display Inspection", NASA Ames Research; 31.1/A.B. Watson, SID 06 Digest, pp. 1312-1315.
Andrew B. Watson, "The Spatial Standard Observer: A new Tool for display metrology tools", Information Display 2007, pp. 1-6.
Yoichi Miyake, et al., "Measurement and Modeling for the Two Dimensional MTF of Human Eye and Its Application for Digital Color Reproduction", Final Program and Proceedings of IS&T and SID Ninth Color Image Conference, Color Science and Engineering; Nov. 6-9, 2001; pp. 153-157.
Toshio Asano, et al., "Automatic Evaluation of White Uniformity for Color CRT Monitors", The Transactions of the Institute of Electronics, Information Communication Engineers DII, Jun. 20, 1990, vol. J73-D-II, No. 6, pp. 830-839 (with English Translation).
Partial Supplementary European Search Report dated Sep. 9, 2016 in European Patent Application No. 14759671.2.
Zhang X et al, "A spatial extension of CIELAB for digital color-image reproduction", SID International Symposium, XP002246662, vol. 5, No. 1, Jan. 1996 (pp. 61-66).
Kunihiko Nagamine et al, "A Quantitative Evaluation Method for Luminance and Color Uniformity of a Display Screen Based on Human Perception", IEICE Transactions on Electronics, Institute of Electronics, XP001579709, vol. E95-C, No. 11, Nov. 2012 (pp. 1699-1706).
Combined Office Action and Search Report dated Aug. 1, 2017 in Chinese Patent Application No. 201480011370.3 (with unedited computer generated English translation of Office Action and English translation of categories of cited documents).

* cited by examiner

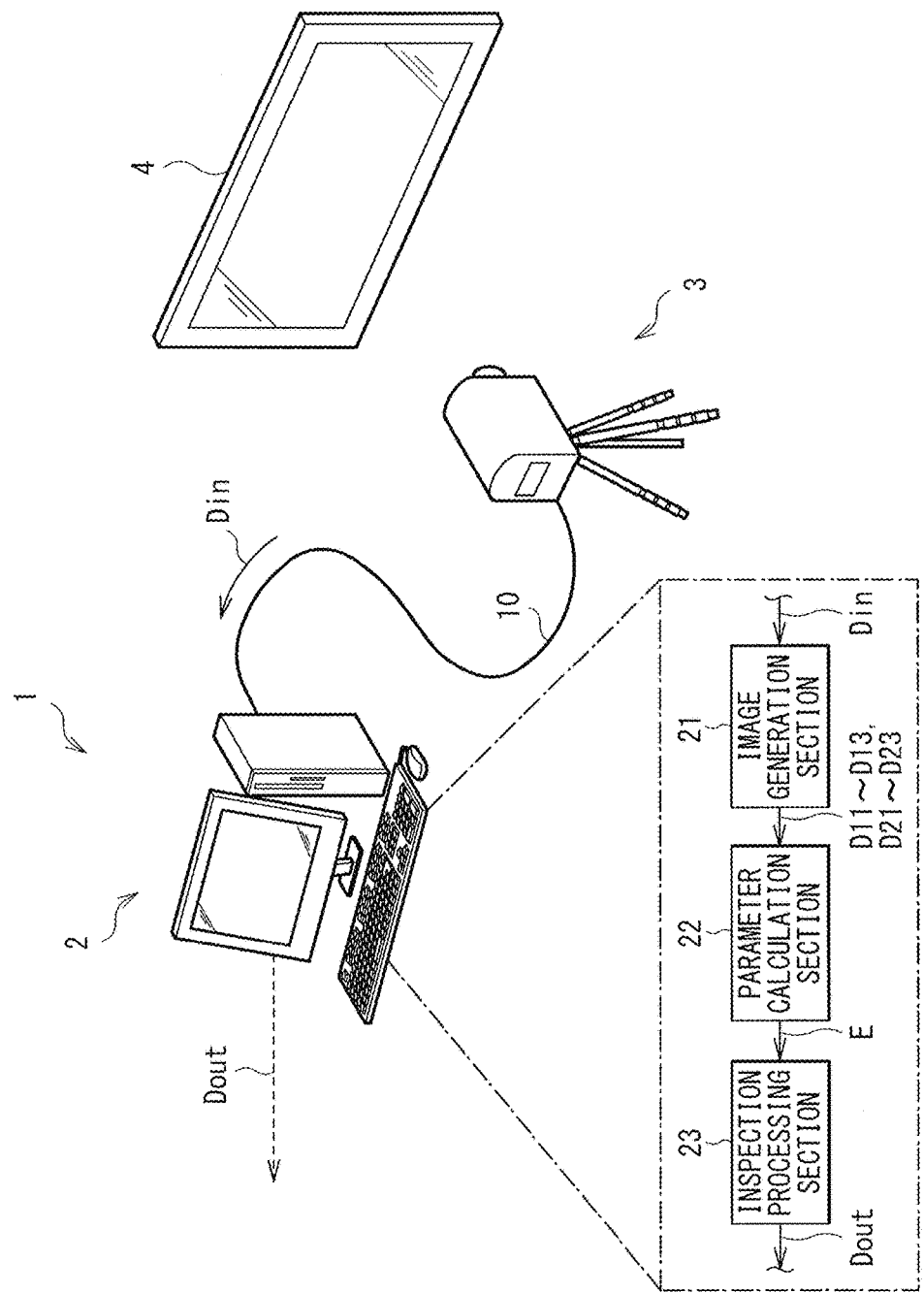
[FIG. 1]

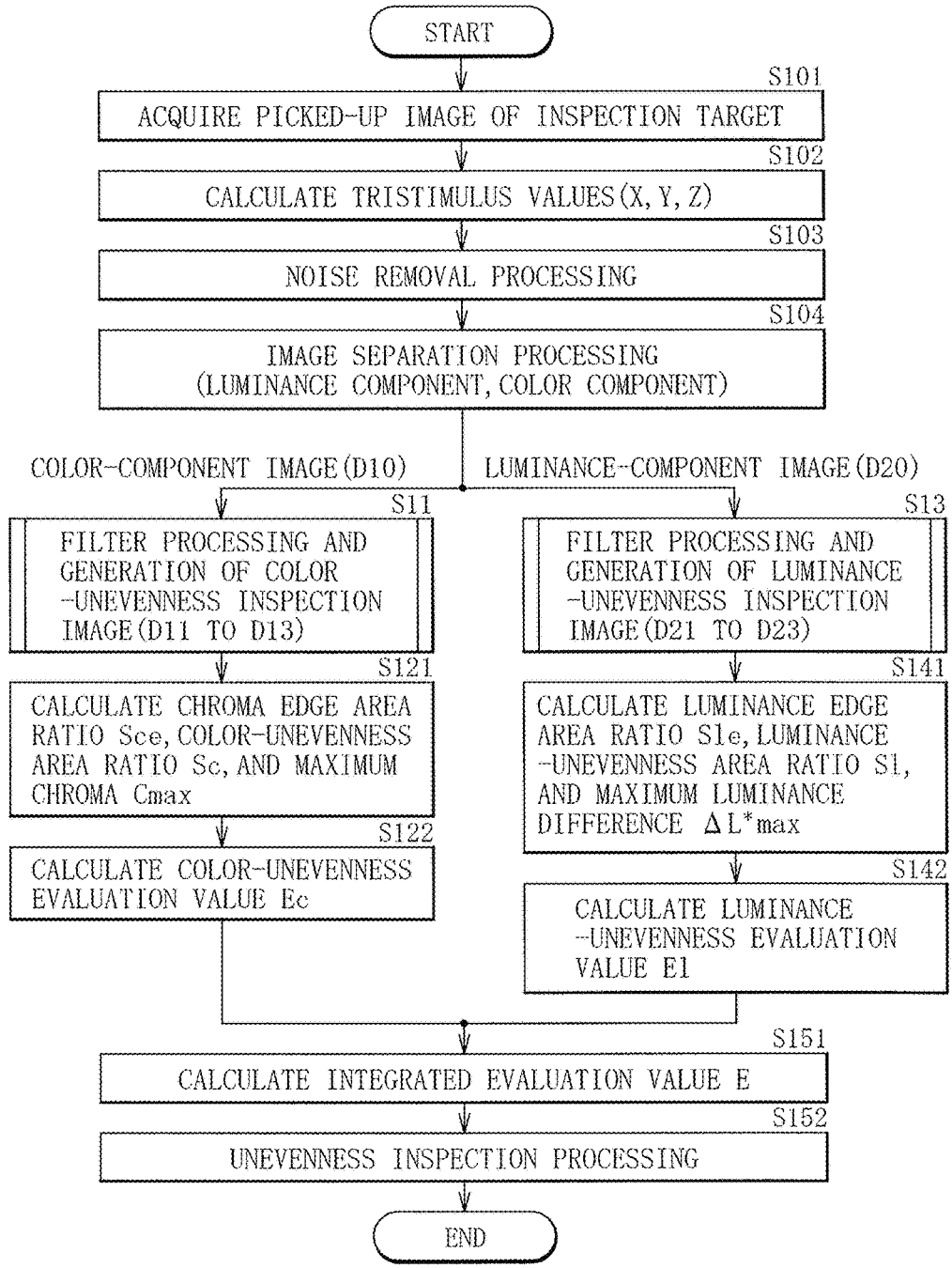

[ FIG. 3 ]
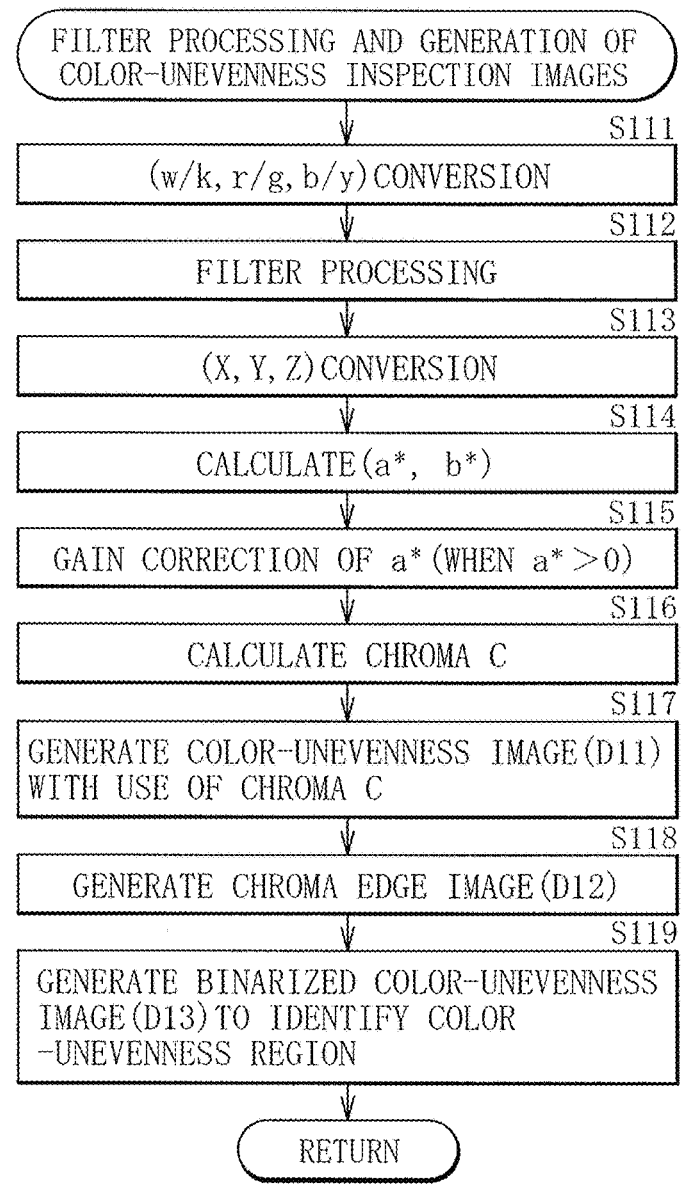

[ FIG. 4 ]
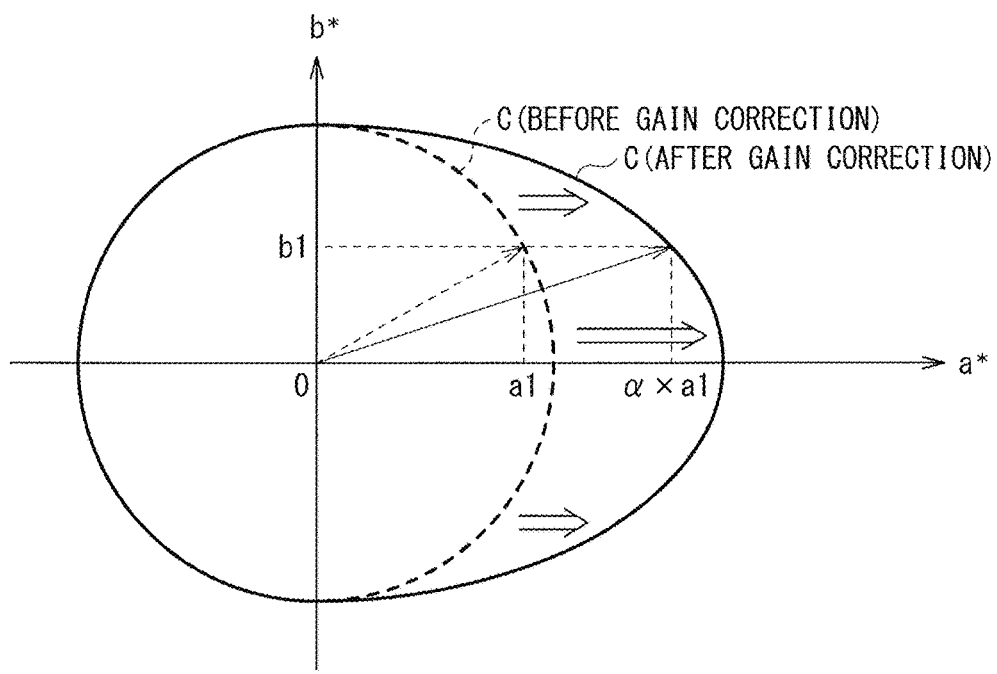

[ FIG. 5A ]
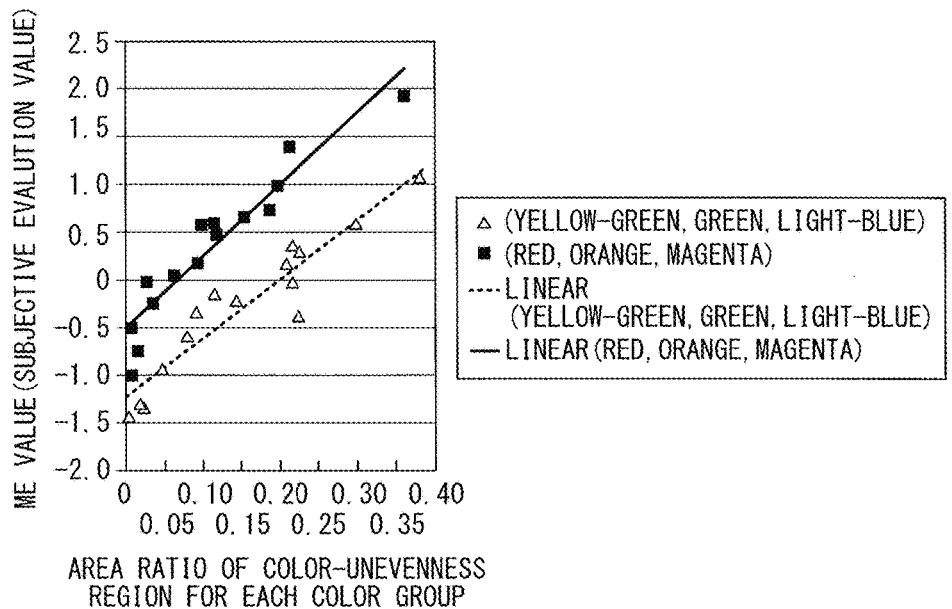
[ FIG. 5B ]
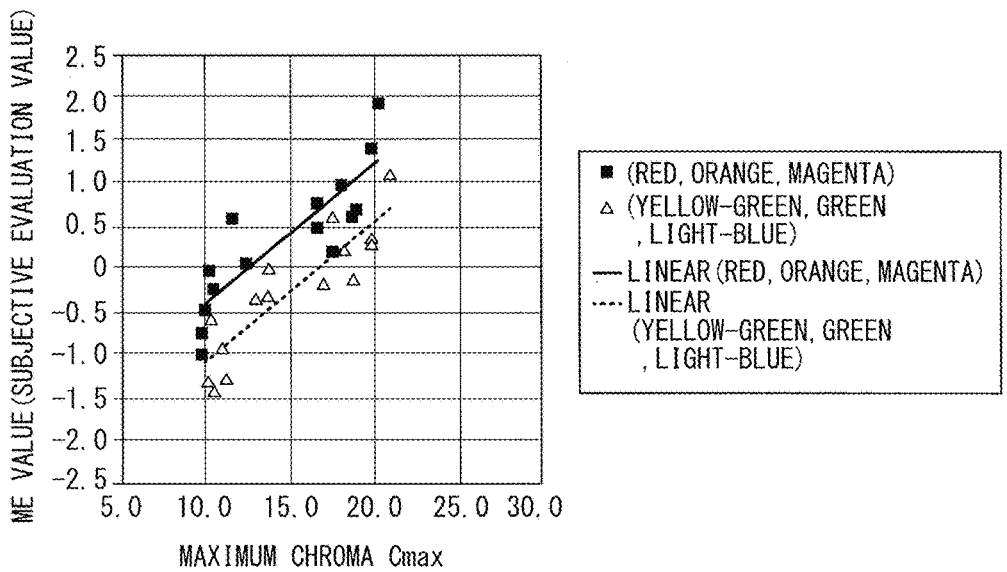

[FIG. 6]
(A) COLOR-UNEVENNESS IMAGE (D11)
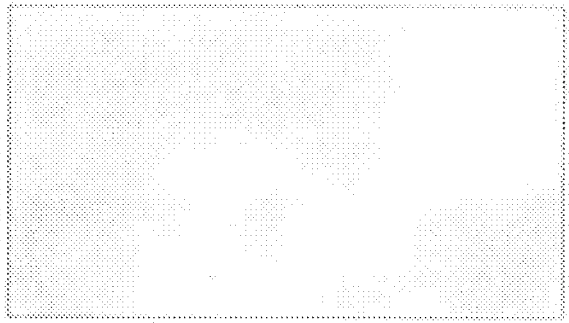
(B) CHROMA EDGE IMAGE (D12)
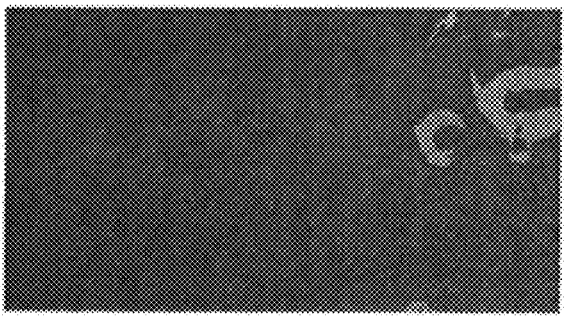
(C) BINARIZED COLOR-UNEVENNESS IMAGE (D13)
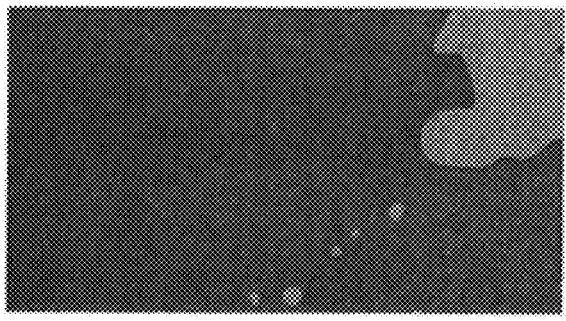
(D) CALCULATION OF MAXIMUM CHROMA Cmax
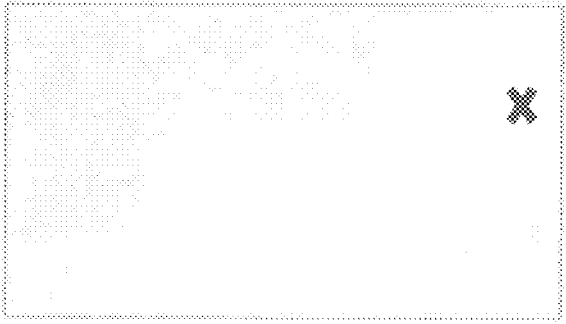

[ FIG. 7 ]
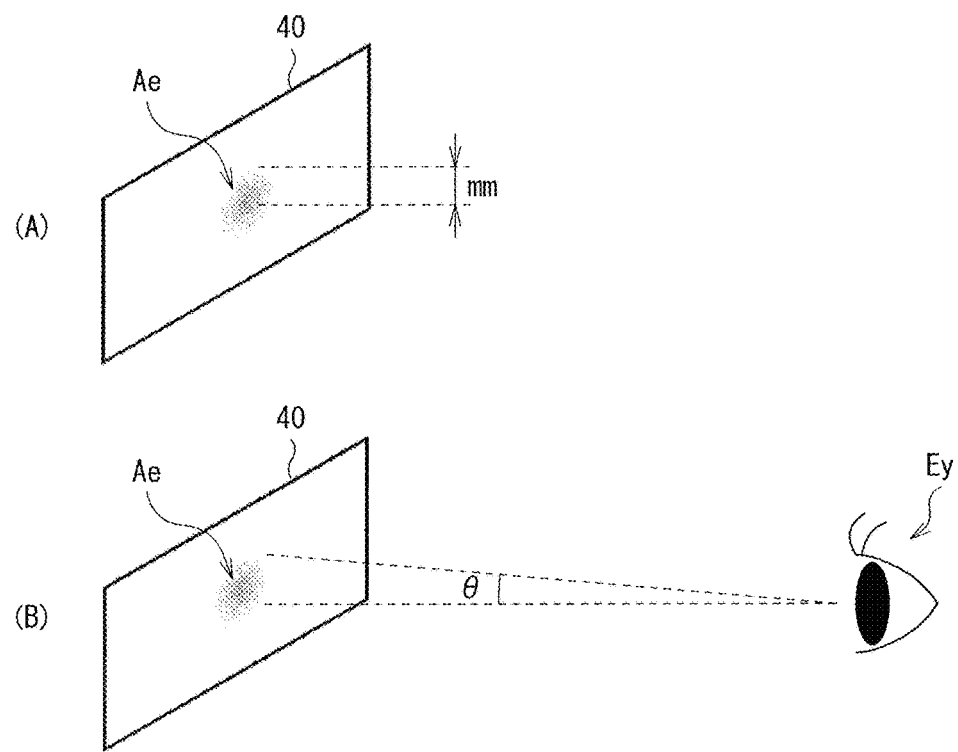

[ FIG. 8 ]
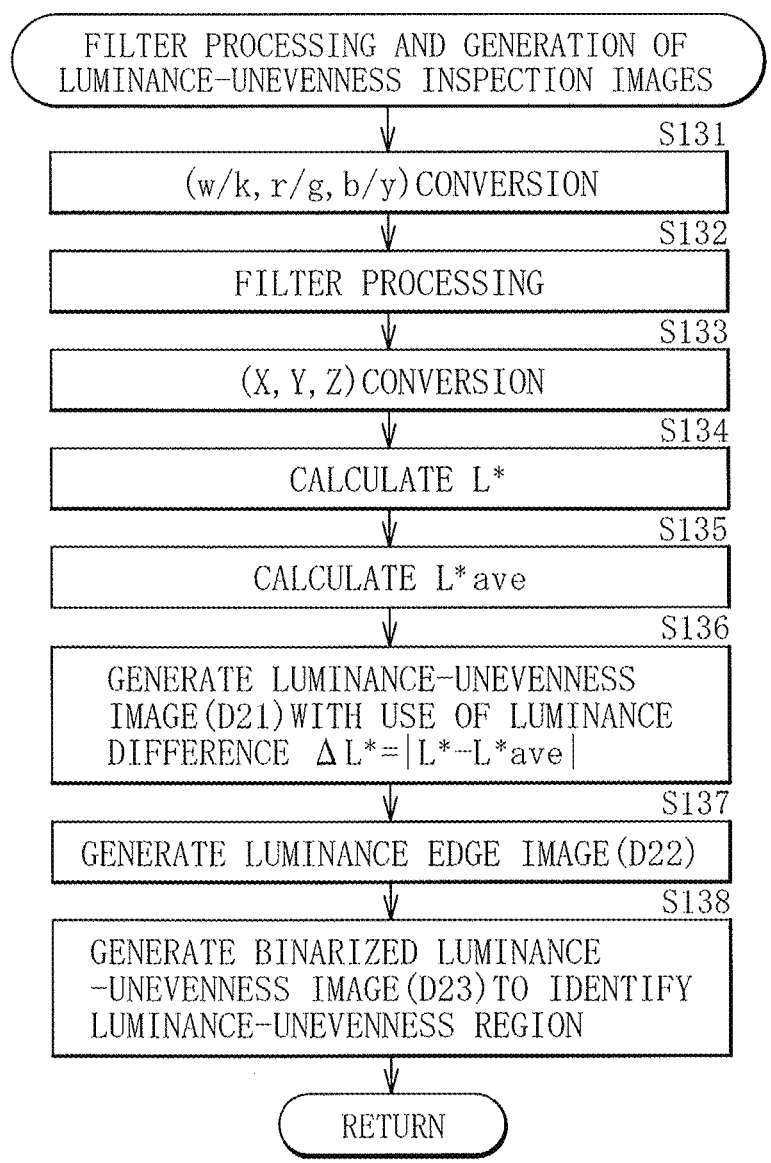

[FIG. 9]
(A) LUMINANCE-UNEVENNESS IMAGE (D21)
(B) LUMINANCE EDGE IMAGE (D22)
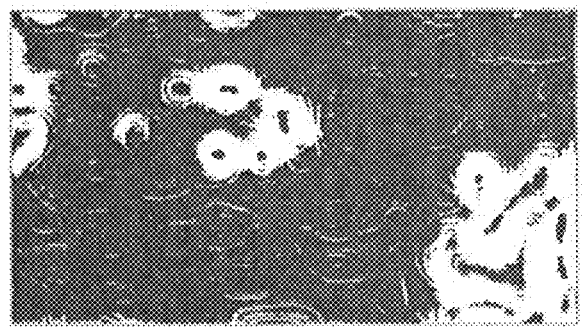
(C) BINARIZED LUMINANCE-UNEVENNESS IMAGE (D23)
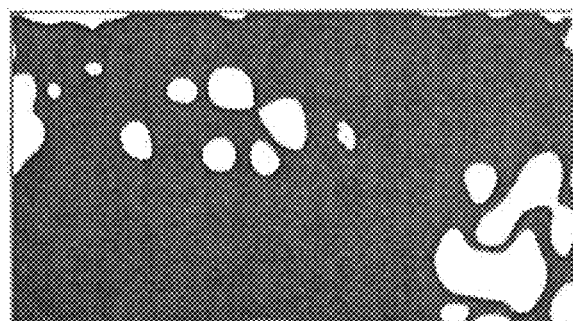
(D) CALCULATION OF MAXIMUM LUMINANCE DIFFERENCE $\Delta L^*max$
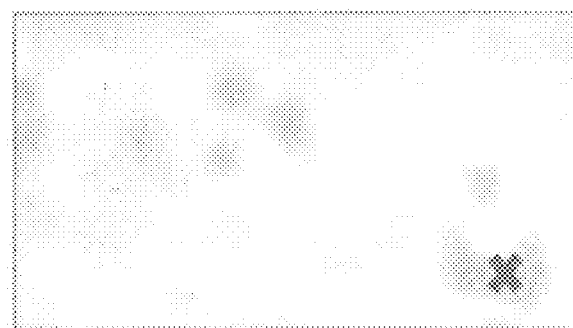

[ FIG. 10 ]
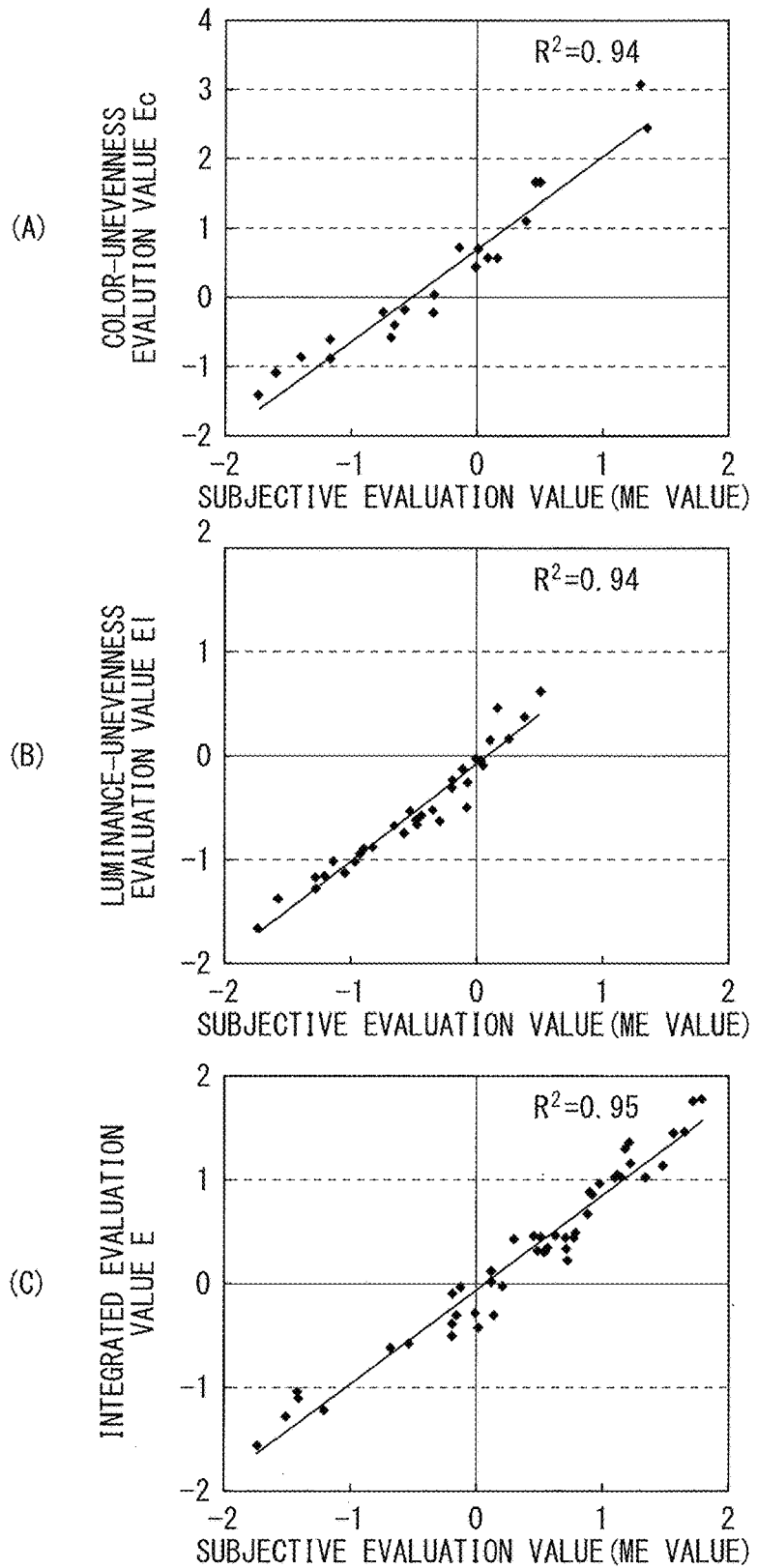

[ FIG. 11 ]
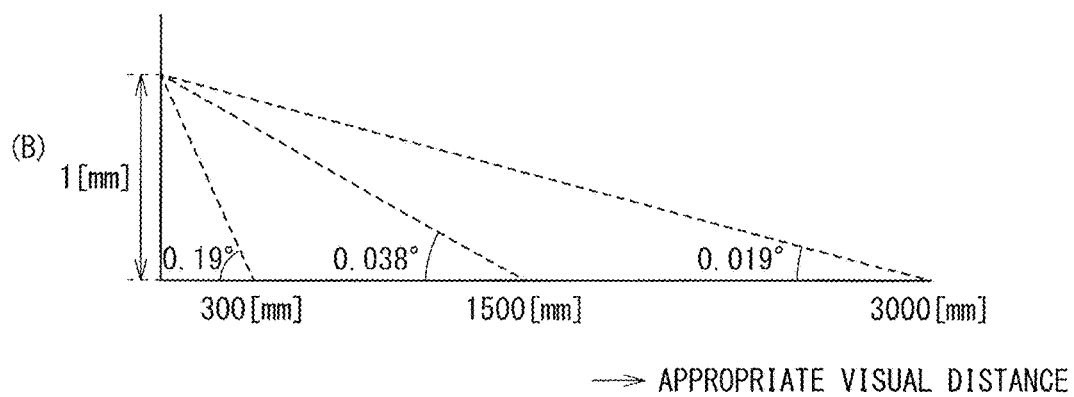

[ FIG. 12 ]

| APPROPRIATE VISUAL DISTANCE (SIZE OF DISPLAY SCREEN) | LUMINANCE EDGE IMAGE (D22) (LUMINANCE EDGE THRESHOLD :dL*/mm=0.5) | LUMINANCE EDGE IMAGE (D22) (LUMINANCE EDGE THRESHOLD :dL*/arcmin=0.218) |
|---|---|---|
| 300[mm] (8[inch]) | | |
| 1500[mm] (40[inch]) | | |
| 3000[mm] (80[inch]) | | |

[FIG. 13]

| INSPECTION TARGET... IMAGE WITHOUT COLOR-UNEVENNESS | COMPARATIVE EXAMPLE (WITHOUT IMAGE SEPARATION PROCESSING FOR SEPARATING LUMINANCE COMPONENT AND COLOR COMPONENT) | EXAMPLE 3 (WITH IMAGE SEPARATION PROCESSING FOR SEPARATING LUMINANCE COMPONENT AND COLOR COMPONENT) |
|---|---|---|
| CHROMA EDGE IMAGE (D12) | × | ○ |
| BINARIZED COLOR-UNEVENNESS IMAGE (D13) | × | ○ |

[ FIG. 14 ]
| INSPECTION TARGET··· IMAGE WITHOUT LUMINANCE-UNEVENNESS | COMPARATIVE EXAMPLE (WITHOUT IMAGE SEPARATION PROCESSING FOR SEPARATING LUMINANCE COMPONENT AND COLOR COMPONENT) | EXAMPLE 3 (WITH IMAGE SEPARATION PROCESSING FOR SEPARATING LUMINANCE COMPONENT AND COLOR COMPONENT) |
|---|---|---|
| LUMINANCE EDGE IMAGE (D22) | ○ 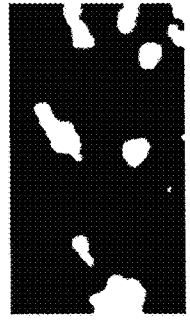 | ○ 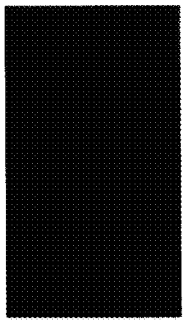 |
| BINARIZED LUMINANCE-UNEVENNESS IMAGE (D23) | × 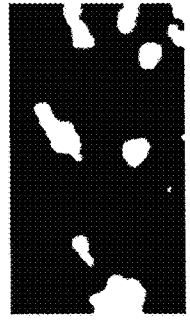 | ○ 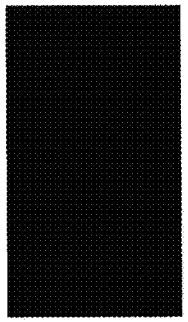 |

[ FIG. 15 ]

| SIZE OF DISPLAY SECREEN[inch] | APPROPRIATE VISUAL DISTANCE[mm] | PITCH OF VISUAL ANGLE 1° [mm] | PITCH OF VISUAL ANGLE 1'° [mm] | PITCH OF 0.1 rad [mm] |
|---|---|---|---|---|
| 8 | 300 | 5.2 | 0.087 | 30.1 |
| 40 | 1500 | 26.2 | 0.436 | 150.5 |
| 80 | 3000 | 52.4 | 0.873 | 301.0 |

(0.1[rad] ≒ 5.73[°])

[ FIG. 16 ]
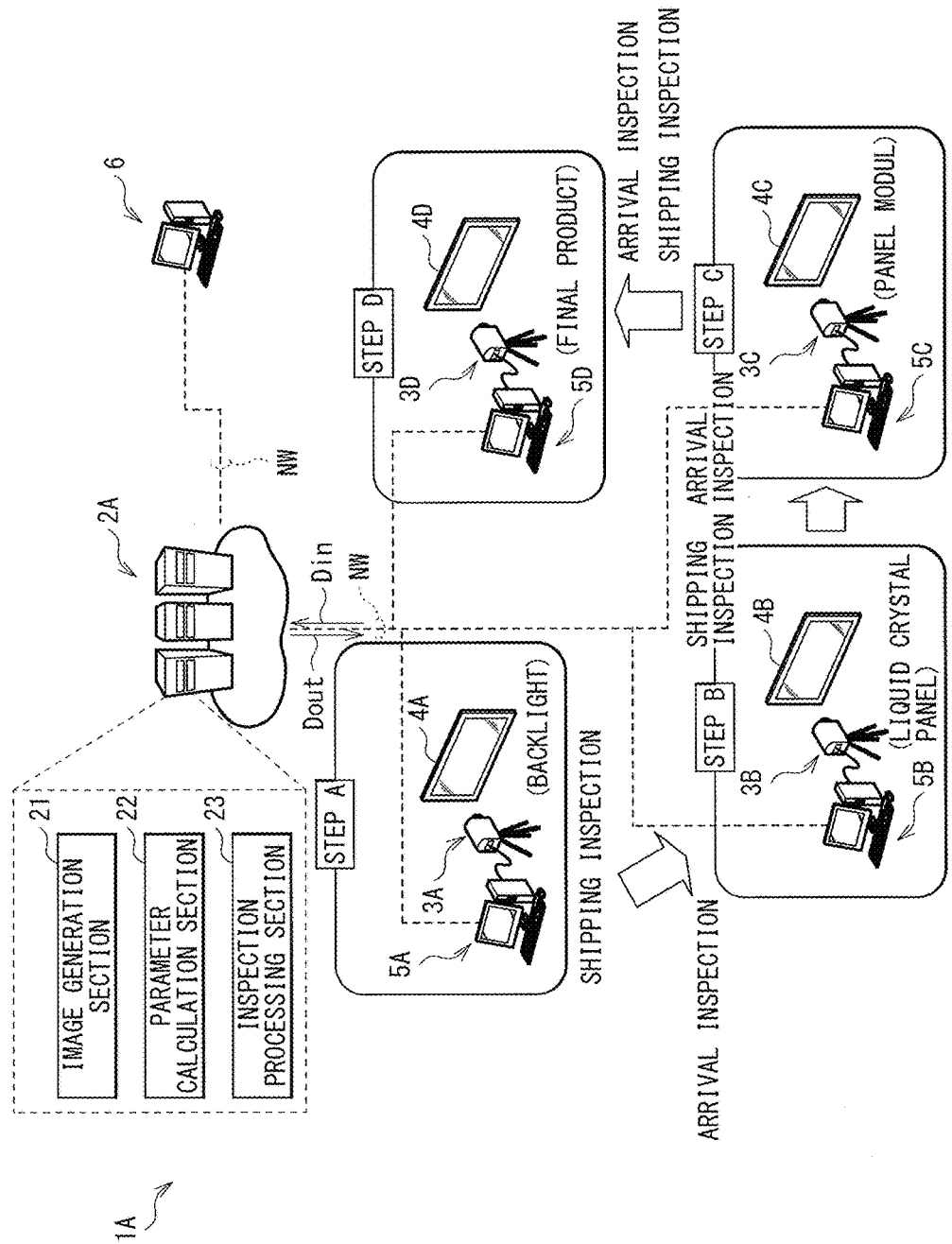

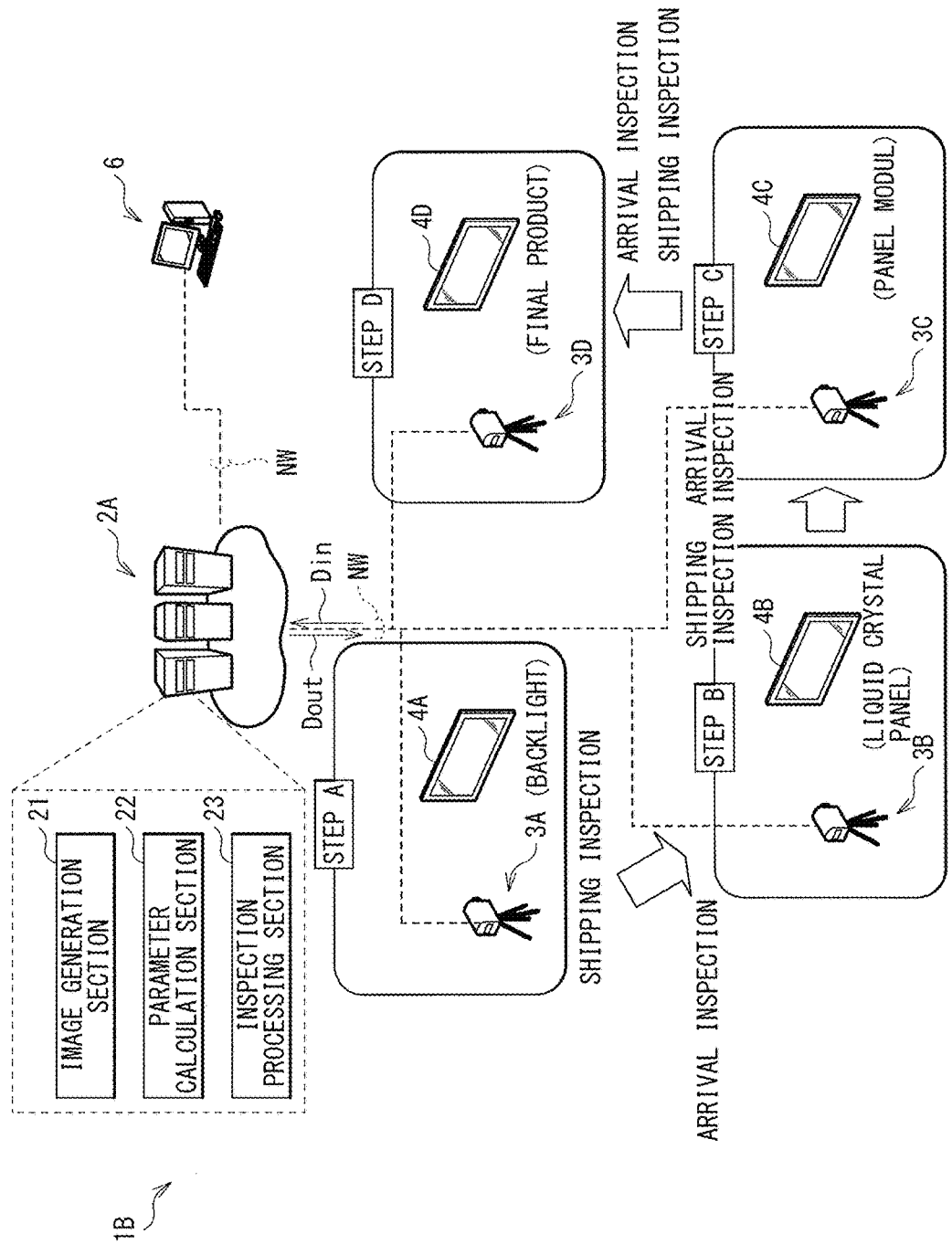
[ FIG. 17 ]

UNEVENNESS INSPECTION SYSTEM, UNEVENNESS INSPECTION METHOD, AND UNEVENNESS INSPECTION PROGRAM

TECHNICAL FIELD

The present disclosure relates to an unevenness inspection system, an unevenness inspection method, and an unevenness inspection program in which unevenness inspection (color-unevenness inspection and luminance-unevenness inspection) in color picture and the like is performed.

BACKGROUND ART

Previously, a color-unevenness inspection and luminance-unevenness inspection in a mass-production process for a display unit that uses a cathode ray tube (CRT), a liquid crystal display (LCD), or the like capable of displaying a color picture, has been mainly performed with use of a sensory test based on a comparison with a boundary sample. This technique is carried out such that a display screen of the display unit as an inspection target is directly viewed by human being and therefore, this is an inspection close to actual use and also a simple and easy technique.

However, this technique relies largely upon the capabilities of individual inspectors, and thus quality of inspection varies depending on factors such as variations among the individual inspectors and the inspector's degree of fatigue. Therefore, it is difficult to perform a stable inspection.

Under the circumstances, there have been proposed some techniques of objective unevenness inspection without depending on the capability of the inspector (for example, PTLs 1 to 5 and NPLs 1 to 3).

CITATION LIST

Patent Literature

PTL 1: Japanese Unexamined Patent Application Publication No. H1-225296
PTL 2: Japanese Unexamined Patent Application Publication No. H10-2800
PTL 3: Japanese Unexamined Patent Application Publication No. 2003-57146
PTL 4: Japanese Unexamined Patent Application Publication No. H10-96681
PTL 5: Japanese Unexamined Patent Application Publication No. 2007-198850

Non-Patent Literature

NPL 1: SID06 DIGEST 31.1
NPL 2: Information Display 2007 1 pp. 2-6
NPL 3: Proc. IS&T and SID Ninth Color Imaging Conference, 2001: pp. 153-157

SUMMARY OF INVENTION

However, in such unevenness inspection, (in the color-unevenness inspection and the luminance-unevenness inspection), typically, further appropriate method is desired, and such method is desirably proposed.

In view of the foregoing, it is desirable to provide an unevenness inspection system, an unevenness inspection method, and an unevenness inspection program capable of performing an appropriate unevenness inspection.

An unevenness inspection system according to an embodiment of the disclosure includes: an image pickup section configured to acquire a picked-up image of an inspection target; an image generation section configured to generate a color-unevenness inspection image and a luminance-unevenness inspection image, based on the picked-up image; a calculation section configured to use both of the color-unevenness inspection image and the luminance-unevenness inspection image to calculate an evaluation parameter; and an inspection section configured to use the calculated evaluation parameter to perform unevenness inspection. The image generation section performs image separation processing to separate a color component and a luminance component on the picked-up image, to generate a color-component image and a luminance-component image, and individually performs filter processing taking account of visual spatial frequency characteristics on the color-component image and the luminance-component image to respectively generate the color-unevenness inspection image and the luminance-unevenness inspection image, based on the filter-processed color-component image and the filter-processed luminance-component image. The calculation section calculates the evaluation parameter in consideration of unevenness visibility with respect to both of color and luminance.

An unevenness inspection method according to an embodiment of the disclosure includes: a step of acquiring a picked-up image of an inspection target; a generation step of generating a color-unevenness inspection image and a luminance-unevenness inspection image, based on the picked-up image; a calculation step of using both of the color-unevenness inspection image and the luminance-unevenness inspection image to calculate an evaluation parameter; and an inspection step of using the calculated evaluation parameter to perform unevenness inspection. In the generation step, image separation processing to separate a color component and a luminance component is performed on the picked-up image to generate a color-component image and a luminance-component image, and filter processing taking account of visual spatial frequency characteristics is individually performed on the color-component image and the luminance-component image to respectively generate the color-unevenness inspection image and the luminance-unevenness inspection image, based on the filter-processed color-component image and the filter-processed unevenness-component image. In the calculation step, the evaluation parameter is calculated in consideration of unevenness visibility with respect to both of color and luminance.

An unevenness inspection program according to an embodiment of the disclosure causes a computer to execute: a step of acquiring a picked-up image of an inspection target; a generation step of generating a color-unevenness inspection image and a luminance-unevenness inspection image, based on the picked-up image; a calculation step of using both of the color-unevenness inspection image and the luminance-unevenness inspection image to calculate an evaluation parameter; and an inspection step of using the calculated evaluation parameter to perform unevenness inspection. In the generation step, image separation processing to separate a color component and a luminance component is performed on the picked-up image to generate a color-component image and a luminance-component image, and filter processing taking account of visual spatial frequency characteristics is individually performed on the color-component image and the luminance-component image to respectively generate the color-unevenness inspection image and the luminance-unevenness inspection image, based on the filter-processed color-component image and the filter-processed luminance-component image. In the calculation step, the evaluation parameter is calculated in consideration of unevenness visibility with respect to both of color and luminance.

In the unevenness inspection system, the unevenness inspection method, and the unevenness inspection program according to the respective embodiments of the disclosure, the color-unevenness inspection image and the luminance-unevenness inspection image are generated based on the picked-up image of the inspection target, the evaluation parameter is calculated with use of both of the color-unevenness inspection image and the luminance-unevenness inspection image, and the unevenness inspection is performed with use of the evaluation parameter. Here, the evaluation parameter is calculated in consideration of unevenness visibility with respect to both of color and luminance. As a result, as compared with the case where the unevenness inspection is performed without considering such visibility, objective unevenness inspection (the color-unevenness inspection and the luminance-unevenness inspection) further matched with human sense is realized. Also, to generate the color-unevenness inspection image and the luminance-unevenness inspection image, the filter processing taking account of visual spatial frequency characteristics is performed after the image separation processing for separating a color component and a luminance component is performed on the picked-up image. As a result, unlike the case where the above-described filter processing is performed without performing such image separation processing, it is possible to avoid occurrence of false color-unevenness component and false luminance-unevenness component, and therefore, more accurate unevenness inspection is realized.

According to the unevenness inspection system, the unevenness inspection method, and the unevenness inspection program of the respective embodiments of the disclosure, when the evaluation parameter is calculated with use of both of the color-unevenness inspection image and the luminance-unevenness inspection image, the calculation is performed in consideration of unevenness visibility to both of color and luminance. Therefore, it is possible to realize objective unevenness inspection further matched with human sense. Moreover, when the color-unevenness inspection image and the luminance-unevenness inspection image are generated, the filter processing taking account of visual spatial frequency characteristics is performed after the image separation processing for separating a color component and a luminance component is performed. Therefore, occurrence of false color-unevenness component and false luminance-unevenness component is avoided, and it is possible to realize more accurate unevenness inspection. Consequently, it becomes possible to perform appropriate unevenness inspection.

BRIEF DESCRIPTION OF DRAWINGS

FIG. 1 is a schematic diagram illustrating an outline configuration example of an unevenness inspection system according to an embodiment of the disclosure, together with a display unit as an inspection target.

FIG. 2 is a flowchart illustrating an example of unevenness inspection processing performed in an image processing apparatus illustrated in FIG. 1.

FIG. 3 is a flowchart illustrating detail of steps in filter processing and generation of color-unevenness inspection images illustrated in FIG. 2.

FIG. 4 is a characteristic diagram illustrating an example of a method of calculating chroma illustrated in FIG. 2.

FIG. 5A is a characteristic diagram illustrating an example of relationship between an area ratio of color-unevenness region for each color group and a subjective evaluation value of color-unevenness.

FIG. 5B is a characteristic diagram illustrating an example of relationship between maximum chroma in a color-unevenness region and a subjective evaluation value of color-unevenness.

FIG. 6A is a diagram illustrating an example of an image produced for color-unevenness inspection processing.

FIG. 6B is a diagram illustrating another example of the image produced for the color-unevenness inspection processing.

FIG. 6C is a diagram illustrating still another example of the image produced for the color-unevenness inspection processing.

FIG. 6D is a diagram illustrating still another example of the image produced for the color-unevenness inspection processing.

FIG. 7 is a schematic diagram for explaining definition of a chroma edge region and a luminance edge region.

FIG. 8 is a flowchart illustrating detail of steps in filter processing and generation of luminance-unevenness inspection images illustrated in FIG. 2.

FIG. 9A is a diagram illustrating an example of an image produced for luminance-unevenness inspection processing.

FIG. 9B is a diagram illustrating another example of the image produced for the luminance-unevenness inspection processing.

FIG. 9C is a diagram illustrating still another example of the image produced for the luminance-unevenness inspection processing.

FIG. 9D is a diagram illustrating still another example of the image produced for the luminance-unevenness inspection processing.

FIG. 10A is a characteristic diagram illustrating relationship between various kinds of subjective evaluation values and a color-unevenness evaluation value according to Example 1.

FIG. 10B is a characteristic diagram illustrating relationship between various kinds of subjective evaluation values and a luminance-unevenness evaluation value according to the Example 1.

FIG. 10C is a characteristic diagram illustrating relationship between various kinds of subjective evaluation values and an integrated evaluation value according to the Example 1.

FIG. 11A is a diagram for explaining an evaluation condition according to Example 2.

FIG. 11B is another diagram for explaining the evaluation condition according to the Example 2.

FIG. 12 is a diagram illustrating luminance edge images according to the Example 2.

FIG. 13 is a diagram illustrating chroma edge images and binarized color-unevenness images according to a comparative example and Example 3.

FIG. 14 is a diagram illustrating luminance edge images and binarized luminance-unevenness images according to the comparative example and the Example 3.

FIG. 15 is a diagram for explaining an effect in a case where a variation per unit visual angle is used as an edge threshold.

FIG. 16 is a schematic diagram illustrating an outline configuration example of an unevenness inspection system according to a modification 1, together with inspection targets.

FIG. 17 is a schematic diagram illustrating an outline configuration example of an unevenness inspection system according to a modification 2, together with inspection targets.

DESCRIPTION OF EMBODIMENTS

Hereinafter, an embodiment of the disclosure is described in detail with reference to drawings. Note that the description will be given in the following order.
1. Embodiment (an example of unevenness inspection in which filter processing is performed after image separation processing for separating a color component and a luminance component)
2. Modifications 1 and 2 (a configuration example in which an image processing function is provided in a server to perform network connection)
3. Other modifications

Embodiment

[Configuration]

FIG. 1 schematically illustrates an outline configuration example of an unevenness inspection system (an unevenness inspection system 1) according to an embodiment of the disclosure, together with a display unit 4 serving as an inspection target. This unevenness inspection system 1 performs integrated unevenness inspection including color-unevenness inspection and luminance-unevenness inspection on a color picture displayed on the display unit 4 or the like, and includes an image processing apparatus 2 and an image pickup apparatus 3 (an image pickup section). Here, as the display unit 4, for example, various types of displays such as a CRT, an LCD, a plasma display panel (PDP), and an organic electro luminescence (EL) display may be applied. Incidentally, an unevenness inspection method and an unevenness inspection program according to respective embodiments of the disclosure are embodied in the unevenness inspection system 1 of the present embodiment, and therefore they will be described together below.

(Image Pickup Apparatus 3)

The image pickup apparatus 3 is used to pick up an image of a display screen (a color display screen) of the display unit 4 that is an inspection target in the above-described unevenness inspection. The image pickup apparatus 3 may be configured using, for example, an image pickup device such as a charge coupled device (CCD) and a complementary metal oxide semiconductor (CMOS). A picked-up image (picked-up image data Din) obtained through the image-pickup by the image pickup apparatus 3 is output to the image processing apparatus 2 through a connecting wire 10. Incidentally, FIG. 1 illustrates a case where the connecting wire 10 is a cable, but the image pickup apparatus 3 and the image processing apparatus 2 may be wirelessly connected to each other.

(Image Processing Apparatus 2)

The image processing apparatus 2 performs the unevenness inspection based on the picked-up image data Din output from the image pickup apparatus 3, and outputs inspection result data Dout as a result of the inspection. The image processing apparatus 2 may be configured using, for example, a personal computer (PC) as illustrated in the figure, or the like. The image processing apparatus 2 includes an image generation section 21, a parameter calculation section 22 (a calculation section), and an inspection processing section 23 (an inspection section).

The image generation section 21 performs predetermined image processing based on the picked-up image data Din, thereby generating color-unevenness inspection images and luminance unevenness inspection images that will be described later. Specifically, the image generation section 21 generates, as the color-unevenness inspection images, a color-unevenness image (color-unevenness image data D11), a chroma edge image (chroma edge image data D12), and a binarized color-unevenness image (binarized color-unevenness image data D13) that are described later. Also, the image generation section 21 generates, as the luminance-unevenness inspection images, a luminance-unevenness image (luminance-unevenness image data D21), a luminance edge image (luminance edge image data D22), and a binarized luminance-unevenness image (binarized luminance-unevenness image data D23) that are described later. To generate the color-unevenness inspection images and the luminance-unevenness inspection images in this way, the image generation section 21 performs predetermined filter processing taking account of visual spatial frequency characteristics after performing image separation processing for separating color component and luminance component described later. Moreover, the image generation section 21 generates the above-described color-unevenness inspection images while performing correction processing (gain correction processing described later) taking account of difference of color-unevenness visibility depending on colors. Note that the detail of the image processing (the image generation processing) by the image generation section 21 will be described later.

The parameter calculation section 22 calculates various kinds of evaluation parameters for the unevenness inspection described later with use of both of the color-unevenness inspection images (the above-described various kinds of image data D11 to D13) and the luminance-unevenness inspection images (the above-described various kinds of image data D21 to D23) that are generated by the image generation section 21. Specifically, the parameter calculation section 23 calculates a color-unevenness evaluation value Ec (color-unevenness parameter) described later with use of the color unevenness inspection images (the various kinds of image data D11 to D13). Also, the parameter calculation section 22 calculates a luminance-unevenness evaluation value El (a luminance-unevenness parameter) described later with use of the luminance-unevenness inspection images (the various kinds of image data D21 to D23). Then, the parameter calculation section 22 weights and adds the color-unevenness evaluation value Ec and the luminance-unevenness evaluation value El to calculate an integrated evaluation value E (an integrated evaluation parameter) as the above-described evaluation parameter. At this time, in the present embodiment, the parameter calculation section 22 calculates the integrated evaluation value E in consideration of unevenness visibility with respect to both of color and luminance. Note that the detail of the calculation processing by the parameter calculation section 22 will also be described later.

The inspection processing section 23 performs the unevenness inspection (the integrated unevenness inspection including the color-unevenness inspection and the luminance-unevenness inspection) of the display screen of the display unit 4 that is the inspection target, with use of the integrated evaluation value E calculated by the parameter calculation section 22. Thus, the inspection result data Dout as the result of the inspection is output from the inspection processing section 23. Note that the detail of the unevenness inspection processing by the inspection processing section 23 will also be described later.

[Action and Effects]

Subsequently, action and effects of the unevenness inspection system 1 according to the present embodiment will be described.

(1. Basic Operation)

In the unevenness inspection system 1, when an image of the display screen of the display unit 4 that is the inspection target is picked up by the image pickup apparatus 3, a picked-up image (the picked-up image data Din) is obtained. The picked-up image data Din is input to the image generation section 21 in the image processing apparatus 2 through the connecting wire 10.

The image generation section 21 performs the predetermined image processing based on the picked-up image data Din to generate the color-unevenness inspection images (the various kinds of image data D11 to D13) and the luminance-unevenness inspection images (the various kinds of image data D21 to D23). Then, the parameter calculation section 22 uses both of the color-unevenness inspection images and the luminance-unevenness inspection images to calculate the integrated evaluation value E that is the evaluation parameter for the unevenness inspection. Then, the inspection processing section 23 uses the integrated evaluation value E to perform the unevenness inspection on the display screen of the display unit 4 that is the inspection target. As a result, the inspection result data Dout as the inspection result is output from the inspection processing section 23.

(2. Detail of Unevenness Inspection Processing)

Next, there will be described the detail of the unevenness inspection processing by the image processing apparatus 2 in the unevenness inspection system 1 according to the present embodiment. FIG. 2 is a flowchart illustrating an example of the unevenness inspection processing performed in the image processing apparatus 2.

(2-1. Preprocessing)

First, as described above, the image generation section 21 obtains the picked-up image (the picked-up image data Din) of the inspection target from the image pickup apparatus 3 through the connecting wire 10 (step S101 in FIG. 2).

Subsequently, the image generation section 21 converts a signal of the picked-up image data Din into a signal (Xi, Yi, Zi) formed of tristimulus values X, Y, and Z (step S102). Specifically, for example, when the picked-up image data Din is a picture signal in sRGB standard, the image generation section 21 performs conversion with use of the following expression (1). Further, when the picked-up image data Din is a picture signal in other standard, the image generation section 21 similarly performs conversion in accordance with such a standard to generate the signal (Xi, Yi, Zi). Incidentally, although the case where the signal of the picked-up image data Din is converted into the signal (Xi, Yi, Zi) is described here, the signal (Xi, Yi, Zi) may be directly obtained by the image pickup apparatus 3.

[Numerical Expression 1]

(when picked-up image data Din is in sRGB standard (based on IEC 61966-2-1))

$$\begin{bmatrix} X_i \\ Y_i \\ Z_i \end{bmatrix} = \begin{bmatrix} 0.4124 & 0.3576 & 0.1805 \\ 0.2126 & 0.7152 & 0.0722 \\ 0.0193 & 0.1192 & 0.9505 \end{bmatrix} \begin{bmatrix} R_{sRGB} \\ G_{sRGB} \\ B_{sRGB} \end{bmatrix} \quad (1)$$

Subsequently, the image generation section 21 performs predetermined noise removal processing as preprocessing on the signal (Xi, Yi, Zi) (step S103). Specifically, for example, the image generation section 21 may use a spatial filter such as Median Filter to perform processing of removing noise caused by a kind of the image pickup apparatus 3 and the image pickup condition. Incidentally, depending on a case, such noise removal processing may not be performed. Further, when the picked-up image data Din is a picture signal in sRGB standard, the image generation section 21 may perform the noise removal processing directly on the picked-up image data Din.

(Image Separation Processing)

Then, the image generation section 21 performs image separation processing for separating a color component and a luminance component described later on the signal (Xi, Yi, Zi) that has been subjected to the noise removal processing, to generate a color-component image (color-component image data D10) and a luminance-component image (luminance-component image data D20) (step S104).

Specifically, the image generation section 21 generates the color-component image data D10 in the following manner, based on the signal (Xi, Yi, Zi) that has been subjected to the noise removal processing. More specifically, the image generation section 21 removes luminance distribution information from the signal (Xi, Yi, Zi) that has been subjected to the noise removal processing, while maintaining color distribution information, to generate the color-component image data D10 that is formed of a signal (XC, YC, ZC). At this time, to remove the luminance distribution information, an average value or a most frequent value of Yi is added to all of the image pickup pixels (display pixels) to calculate YC. Incidentally, the value to be added is not limited to the average value or the most frequent value of Yi, and may be a constant value. Moreover, to maintain the color distribution information, the above-described YC is used to calculate XC and ZC so that the values (a*, b*) calculated from (X, Y, Z) signal by using the following expression (2) are not changed.

Here, the values (a*, b*) are values in the CIE 1976 L*a*b* color space (CIELAB color space) recommended by the Commission International de l'Éclairage (CIE) in 1976. The CIELAB color space is recommended as a uniform color space and is a space in consideration of uniformity with respect to human's visual perception of colors. Further, Xn, Yn and Zn in the expression (2) are tristimulus values of a perfect reflecting diffuser.

[Numerical Expression 2]

$$\begin{cases} L^* = 116 f(Y/Y_n) - 16 \\ a^* = 500[f(X/X_n) - f(Y/Y_n)] \\ b^* = 200[f(Y/Y_n) - f(Z/Z_n)] \end{cases} \quad (2)$$

$$\text{where, } f(t) = \begin{cases} t^{1/3} & (t > (6/29)^3) \\ \frac{1}{3}\left(\frac{29}{6}\right)^3 t + \frac{4}{29} & (\text{otherwise}) \end{cases}$$

More specifically, the image generation section 21 uses the following expressions (3) and (4) to calculate XC and ZC.

$$500 \times [f(Xi/Xn) - f(Yi/Yn)] = 500 \times [f(XC/Xn) - f(YC/Yn)] \quad (3)$$

so that a*(Xi,Yi,Zi)=a*(XC,YC,ZC)

$$200 \times [f(Yi/Yn) - f(Zi/Zn)] = 200 \times [f(YC/Yn) - f(ZC/Zn)] \quad (4)$$

so that b*(Xi, Yi, Zi)=b*(XC,YC,ZC)

On the other hand, the image generation section 21 generates the luminance-component image data D20 in the following manner, based on the signal (Xi, Yi, Zi) that has been subjected to the noise removal processing. Specifically, the image generation section 21 removes the color distribution information from the signal (Xi, Yi, Zi) that has been subjected to the noise removal processing, while maintaining the luminance distribution information, to generate the luminance-component image data D20 that is formed of a signal (XL, YL, ZL). At this time, to maintain the luminance distribution information, the value of Yi is added as is to all of the image pickup pixels (display pixels) to calculate YL. Further, to remove the color distribution information, the above-described YL is used to calculate XL and ZL so that the above-described values (a*, b*) become 0 (zero).

More specifically, the image generation section 21 uses the following expressions (5) and (6) to calculate XL and ZL.

$$500\times[f(XL/Xn)-f(YL/Yn)]=0 \tag{5}$$

so that a*(XL, YL, ZL)=0

$$200\times[f(YL/Yn)-f(ZL/Zn)]=0 \tag{6}$$

so that b*(XL,YL,ZL)=0

(2-2. Filter Processing and Generation of Color-Unevenness Inspection Image)

Subsequently, the image generation section 21 performs predetermined filter processing on the color-component image (the color-component image data D10) thus generated, and generates the color-unevenness inspection images (the various kinds of image data D11 to D13) based on the filter-processed color-component image data D10 (step S11).

FIG. 3 is a flowchart illustrating the detail of the steps (steps S111 to S119) in the filter processing and the generation of the color-unevenness inspection images.

(Filter Processing)

At this step, first, the image generation section 21 performs (w/k, r/g, b/y) conversion that is defined by the following expression (7), on the color-component image data D10 formed of the signal (XC, YC, ZC) (step S111 in FIG. 3). As a result, the color-component image data D10 is converted from (X, Y, Z) coordinate system to (w/k, r/g, b/y) coordinate system. Then, 2D Fourier transform for every three axes (components) is performed on coordinate-converted (w/k, r/g, b/y) signal to develop the coordinate-converted color-component image data D10 to spatial frequency. Note that (w/k) indicates (white/black), (r/g) indicates (red/green), and (b/y) indicates (blue/yellow).

[Numerical Expression 3]

$$\begin{bmatrix} w/k \\ r/g \\ b/y \end{bmatrix} = \begin{bmatrix} 0.279 & 0.720 & -0.107 \\ -0.449 & 0.290 & -0.077 \\ 0.086 & -0.590 & 0.501 \end{bmatrix} \begin{bmatrix} X \\ Y \\ Z \end{bmatrix} \tag{7}$$

Subsequently, the image generation section 21 performs filter processing taking account of visual spatial frequency characteristics (contrast sensitivity factor) on the 2D-Fourier-transformed data (step S112). Here, the visual spatial frequency characteristics are determined by subjective evaluation experiment, and are defined by opposite color space by human object recognition and corresponds to three axes of (w/k, r/g, b/y). Performing filter processing taking account of such visual spatial frequency characteristics makes it possible to perform processing to allow the image to be close to human sensitivity. Note that, after the filter processing, 2D inverse Fourier transform is performed to return the filter-processed data D10 to (w/k, r/g, b/y) coordinate system.

Next, the image generation section 21 performs (X, Y, Z) conversion defined by the following expression (8), on the filter-processed (w/k, r/g, b/y) signal (step S113). As a result, the coordinate conversion from (w/k, r/g, b/y) coordinate system to (X, Y, Z) coordinate system is performed.

[Numerical Expression 4]

$$\begin{bmatrix} X \\ Y \\ Z \end{bmatrix} = \begin{bmatrix} 0.626554504 & -1.867177598 & -0.153156373 \\ 1.36985545 & 0.934755824 & 0.436229005 \\ 1.505650755 & 1.421323772 & 2.53602108 \end{bmatrix} \begin{bmatrix} w/k \\ r/g \\ b/y \end{bmatrix} \tag{8}$$

In this way, in the present embodiment, after the image separation processing for separating the color component and the luminance component is performed on the picked-up image data Din, the filter processing taking account of visual spatial frequency characteristics is performed. As a result, unlike the case where the above-described filter processing is performed without such image separation processing, it is possible to avoid occurrence of false color-unevenness component, and to realize more accurate unevenness inspection.

The reason why the such false color-unevenness component occurs is as follows. Specifically, in the spatial frequency characteristics in the above-described filter processing, (w/k) that is an axis of the luminance component and (r/g) and (b/y) that are axes of the color component are largely different in low frequency characteristics from each other. Further, as illustrated in the above-described expression (2), L* is basically calculated from only the value Y, whereas the value Y is also used in calculation of the values (a*, b*). Accordingly, if the value Y that is largely influenced by (w/k) subjected to the filter processing that is largely different in visual spatial frequency characteristics is used, color distribution information that does not ordinary exist is generated, and false color-unevenness easily occurs in the image. Accordingly, in the present embodiment, the filter processing taking account of visual spatial frequency characteristics is performed after the image separation processing is performed as described above, to avoid occurrence of false color-unevenness component caused by difference between the spatial frequency characteristics (low frequency characteristics) of the color component and the spatial frequency characteristics of the luminance component.

Subsequently, the image generation section 21 uses the above-described expression (2) to calculate the above-described values (a*, b*), based on the signal (X, Y, Z) that is obtained through the above-described (X, Y, Z) conversion (step S114).

Next, the image generation section 21 generates the above-described various kinds of color-unevenness inspection images while performing correction processing (the gain correction processing) taking account of difference of color-unevenness visibility depending on colors, in each of the image pickup pixels. Specifically, the image generation section 21 calculates chroma C while performing such correction processing in each of the image pickup pixels. More specifically, first, the image generation section 21 performs the gain correction processing (the correction processing using gain α) represented by the following expression (9) as the correction processing taking account of difference of the color-unevenness visibility on the value a* calculated at the step S114 (step S115). Then, the image generation section 21 uses the values (a*', b*) calculated at the steps S114 and S115 to calculate the chroma C for each of the image pickup pixels by the following expression (10) (step S116).

$$a^{*\prime} = (\alpha \times a^*) \quad (9)$$
(For $a^* > 0$: gain $\alpha > 1$, for $a^* \leq 0$: gain $\alpha = 1$ $$C = \{(a^{*\prime}) + (b^*)^2\}^{1/2} \quad (10)$$
$$= \{(\alpha \times a^*)^2 + (b^*)^2\}^{1/2}$$

Such gain correction processing corresponds to conversion (correction) of a point of (a*, b*)=(a1, b1) into a point of (a*, b*)=(α×a1, b1), considering (a*, b*) coordinate system as illustrated in FIG. 4. Accordingly, a curve illustrating the chroma C before and after the gain correction processing is as illustrated in FIG. 4. Specifically, the curve illustrating the chroma C before the gain correction processing is circular, whereas the curve illustrating the chroma C after the gain correction processing is not circular but ellipsoidal in a region of a*>0 as illustrated by an arrow in FIG. 4.

Here, the reason why the chroma C is calculated after such gain correction processing is performed is as follows. Specifically, this is because visibility of color-unevenness (color-unevenness visibility) perceived by human being varies depending on a kind of color configuring the color-unevenness.

More specifically, first, the color-unevenness visibility (ME value, subjective evaluation value of unevenness (here, color-unevenness) by human being) varies depending on an area ratio of color-unevenness region for each color group (an area ratio of color-unevenness region for each color group with respect to entire region of the inspection target (entire display pixel region in the display screen)). In other words, for example, as illustrated in FIG. 5A, in the area ratio of a color group corresponding to colors of red (R), orange (R), and magenta (M), the ME value (the color-unevenness visibility) at a certain area ratio becomes higher as compared with the area ratio of a color group corresponding to colors of yellow green (YG), green (G), and light blue (LB).

Further, the color-unevenness visibility (the ME value) varies depending on a color group to which the color exhibiting a maximum chroma Cmax (maximum chroma in the entire color-unevenness region) described later belongs. In other words, for example, as illustrated in FIG. 5B, when a color belonging to a color group corresponding to colors of red (R), orange (O), and magenta (M) exhibits the maximum chroma Cmax, the ME value (the color-unevenness visibility) at the same maximum chroma Cmax becomes higher as compared with the case where a color belonging to a color group corresponding to colors of yellow green (YG), green (G), and light blue (LB) exhibits the maximum chroma Cmax.

Therefore, in the present embodiment, the image generation section 21 calculates the chroma C while performing the gain correction processing taking account of difference of color-unevenness visibility depending on colors as described above. Specifically, the image generation section 21 performs the correction (the gain correction) to selectively increase the value a*, on the region of a*>0 that corresponds to the color group whose color-unevenness visibility is relatively high (the color group corresponding to colors of red (R), orange (O), and magenta (M)). As a result, as compared with the case where the unevenness inspection (the color-unevenness inspection) is performed without taking account of the difference of the color-unevenness visibility depending on colors, objective unevenness inspection further matched with human sense is realized.

(Generation of Color-Unevenness Inspection Image)

Next, the image generation section 21 uses the chroma C thus calculated to generate a color-unevenness image (the color-unevenness image data D11) that is one of the color-unevenness inspection images, from the picked-up image (step S117). Specifically, the image generation section 21 generates the color-unevenness image configured of the value of the chroma C for each of the image pickup pixels. As a result, for example, the color-unevenness image configured of the color-unevenness image data D11 as illustrated in FIG. 6A may be generated.

Then, the image generation section 21 also uses the calculated chroma C to generate the chroma edge image (the chroma edge image data D12) that is one of the color-unevenness inspection images, from the picked-up image (step S118). Specifically, for example, the image generation section 21 may perform Sobel filter processing or the like to identify the chroma edge region, and accordingly generates the chroma edge image. As a result, the chroma edge image configured of the chroma edge image data D12 as illustrated in FIG. 6B may be generated.

Here, the chroma edge region identified at this time may be defined as, for example, a region in which chroma variation (chroma edge intensity) per unit length in the inspection target (the display screen) or chroma variation per unit visual angle is equal to or greater than a predetermined threshold (a chroma edge threshold). Specifically, for example, as illustrated in (A) of FIG. 7, a region (for example, a region Ae in (A) of FIG. 7) whose chroma variation per unit length is equal to or greater than the chroma edge threshold (for example, (dC*/mm)=2.0) is identified as the chroma edge region. This chroma edge threshold is defined with respect to unit length on a display screen 40 so as to match with sensitivity of color-unevenness perceived by human being. Alternatively, for example, as illustrated in (B) of FIG. 7, a region (for example, the region Ae in (B) of FIG. 7) whose chroma variation per unit visual angle is equal to or greater than the chroma edge threshold (for example, (dC*/arcmin)=0.873) is identified as the chroma edge region. This chroma edge threshold is defined with respect to unit visual angle θ by an observer (an eye Ey) so as to match with sensitivity of color-unevenness perceived by human being. Note that, as the visual angle θ at this time, for example, the visual angle defined in the following manner may be desirably used. Specifically, when the eyesight of human being is 1.0, resolution of the angle identified by human being is defined as one arc-minute that is one-sixtieth of one degree. Therefore, the visual angle θ defined with use of one arc-minute in consideration of such visual characteristics of human being may be desirably used. The same applies to the following description, however the definition is not limited thereto.

Subsequently, further, the image generation section 21 uses the generated color-unevenness image (the color-unevenness image data D11) to generate the binarized color-unevenness image (the binarized color-unevenness image data D13), and identifies the color-unevenness region (step S119). At this time, the image generation section 21 identifies the color-unevenness region based on the intensity of the chroma C in each of the image pickup pixels. Specifically, the image pickup pixel in which the value of the chroma C is equal to or greater than the predetermined threshold (for example, 2.0) is identified as the image pickup pixel belonging to the color-unevenness region. On the other hand, the image pickup pixel in which the value of the chroma C is smaller than the above-described threshold is identified as the image pickup pixel not belonging to the color-unevenness region. Thus, the image generation section 21 identifies the color-unevenness region. As a result, for example, as the binarized color-unevenness image (the binarized color-unevenness image data D13) illustrated in FIG. 6C, the color-unevenness region may be identified. Note that, in the binarized color-unevenness image illustrated in FIG. 6C, the color-unevenness region is illustrated by red, and other regions are illustrated by black (the image illustrated in FIG. 6C is the binarized image).

(2-3. Calculation of Color-Unevenness Evaluation Value Ec)

Subsequently, the parameter calculation section 22 calculates the color-unevenness evaluation value Ec in the following manner (steps S121 to S122 in FIG. 2).

First, the parameter calculation section 22 uses the various kinds of color-unevenness inspection images (the color-unevenness image data D11, the chroma edge image data D12, and the binarized color-unevenness image data D13) generated in the above manner, to calculate various kinds of parameters described below (step S121).

Specifically, the parameter calculation section 22 uses the chroma edge image (the chroma edge image data D12) to calculate a chroma edge area ratio Sce that is an area ratio of the chroma edge region with respect to the entire region of the inspection target (the entire display pixel region in the display screen).

Further, the parameter calculation section 22 uses the binarized color-unevenness image (the binarized color-unevenness image data D13) to calculate a color-unevenness area ratio Sc that is an area ratio of the color-unevenness region with respect to the entire region of the inspection target (the entire display pixel region in the display screen).

Furthermore, the parameter calculation section 22 uses the color-unevenness image (the color-unevenness image data D11) to calculate the maximum chroma Cmax in the entire color-uneven region. For example, in the example of the color-unevenness image illustrated in FIG. 6A, the maximum chroma Cmax is exhibited in the image pickup pixel indicated by a symbol "x" in FIG. 6D.

Then, the parameter calculation section 22 weights and adds the chroma edge area ratio Sce, the color-unevenness area ratio Sc, and the maximum chroma Cmax that are thus calculated, to calculate the color-unevenness evaluation value Ec (step S122). Specifically, the parameter calculation section 22 may use, for example, the following expression (11) to calculate the color-unevenness evaluation value Ec. Note that, in the expression (11), each of constants (coefficients) k1, k2, and k3 represents a weighting coefficient, and c1 represents a predetermined constant (including 0 (zero)).

$$Ec = k1 \times Sce + k2 \times Sc + k3 \times Cmax + c1 \quad (11)$$

(2-4. Filter Processing and Generation of Luminance-Unevenness Inspection Image)

Also, the image generation section 21 performs the following processing on the luminance-component image (the luminance-component image data D20) generated at the above-described step S104 (in the image separation processing). Specifically, the image generation section 21 performs the above-described predetermined filter processing, and generates the luminance-unevenness inspection images (the various kinds of image data D21 to D23) based on the filter-processed luminance-component image data D20 (step S13).

FIG. 8 is a flowchart illustrating the detail of steps (steps S131 to S138) in the filter processing and the generation of the luminance-unevenness inspection images.

(Filter Processing)

At this step, first, the image generation section 21 performs (w/k, r/g, b/y) conversion defined by the above-described expression (7), on the luminance-component image data D20 formed of the signal (XL, YL, ZL) (step S131 in FIG. 8). As a result, the luminance-component image data D20 is converted from (X, Y, Z) coordinate system to (w/k, r/g, b/y) coordinate system. Then, 2D Fourier transform for every three axes is performed on the coordinate-converted (w/k, r/g, b/y) signal to develop the coordinate-converted luminance-component image data D20 to spatial frequency.

Then, the image generation section 21 performs the filter processing taking account of visual spatial frequency characteristics on the 2D-Fourier-transformed data, in a manner similar to the above-described step S112 (step S132). Note that, after the filter processing, 2D inverse Fourier transform is performed to return the data to (w/k, r/g, b/y) coordinate system.

Next, the image generation section 21 performs (X, Y, Z) conversion defined by the above-described expression (8), on the filter-processed signal (w/k, r/g, b/y) (step S133). As a result, the filter-processed (w/k, r/g, b/y) signal is converted from (w/k, r/g, b/y) coordinate system to (X, Y, Z) coordinate system.

Also here, in the present embodiment, after the image separation processing for separating the color component and the luminance component is performed on the picked-up image data Din, the filter processing taking account of the visual spatial frequency characteristics is performed. Accordingly, unlike the case where the above-described filter processing is performed without performing such image separation processing, occurrence of false luminance-unevenness component caused by difference of the spatial frequency characteristics (the low frequency characteristics) between the color component and the luminance component is avoided, which makes it possible to realize more accurate unevenness inspection.

Then, the image generation section 21 calculates L* (luminosity), based on the signal (X, Y, Z) obtained through the above-described (X, Y, Z) conversion (step S134). Specifically, the image generation section 21 uses the above-described expression (2) to calculate the luminance L* for each of the image pickup pixels.

Subsequently, the image generation section 21 calculates average luminance L*ave that is an average value of the luminance L* in the entire region of the white image (in this case, the entire display pixel region of the white image displayed on the display screen of the display unit 4) (step S135).

(Generation of Luminance-Unevenness Inspection Image)

Then, the image generation section 21 uses the luminance L* and the average luminance L*ave that have been calculated in this way, to generate the luminance-unevenness image (the uneven-luminance image data D21) that is one of the luminance-unevenness inspection images from the picked-up image (step S136). Specifically, the image generation section 21 calculates luminance difference ΔL*

(=|L*−L*ave|) that is an absolute value of a difference between the luminance L* for each of the image pickup pixels and the average luminance L*ave, and generates luminance-unevenness image that is formed of the luminance difference ΔL*. As a result, the luminance-unevenness image formed of the luminance-unevenness image data D21, for example, as illustrated in FIG. 9A may be generated. Incidentally, at this time, the luminance-unevenness image may be generated with use of the value of the luminance L* instead of the luminance difference ΔL* as described above.

Subsequently, the image generation section 21 also uses the calculated luminance L* to generate the luminance edge image (the luminance edge image data D22) that is one of the luminance-unevenness inspection images, from the picked-up image (step S137). For example, the image generation section 21 may perform, for example, Sobel filter processing or the like to identify the luminance edge region, and then generates the luminance edge image. As a result, the luminance edge image formed of the luminance edge image data D22, for example, as illustrated in FIG. 9B may be generated.

Here, the luminance edge region identified at this time may be defined, for example, as a region in which luminance variation (luminance edge intensity) per unit length in the inspection target (the display screen) or luminance variation per unit visual angle is equal to or greater than a predetermined threshold (a luminance edge threshold). Specifically, also here, for example, as illustrated in (A) of FIG. 7, a region (for example, the region Ae in (A) of FIG. 7) whose luminance variation per unit length is equal to or greater than the luminance edge threshold (for example, (dL*/mm)=0.5) is identified as the luminance edge region. This luminance edge threshold is defined with respect to unit length on the display screen 40. Alternatively, for example, as illustrated in (B) of FIG. 7, a region (for example, the region Ae in (B) of FIG. 7) whose luminance variation per unit visual angle is equal to or greater than the luminance edge threshold (for example, (dL*/arcmin)=0.218) is identified as the luminance edge region. This luminance edge threshold is defined with respect to unit visual angle θ by an observer (an eye Ey)

Subsequently, the image generation section 21 further uses the generated luminance-unevenness image (the luminance-unevenness image data D21) to generate the binarized luminance-unevenness image (the binarized luminance-unevenness image data D23), and then identifies the luminance-unevenness region (a bright and dark region) (step S138). At this time, the image generation section 21 identifies the luminance-unevenness region based on level of the luminance difference ΔL* in each of the image pickup pixels. Specifically, the image pickup pixel in which the value of the luminance difference ΔL* is equal to or greater than the predetermined threshold (for example, 0.3) is identified as the image pickup pixel belonging to the luminance-unevenness region. On the other hand, the image pickup pixel in which the value of the luminance difference ΔL* is smaller than the above-described threshold is identified as the image pickup pixel not belonging to the luminance-unevenness region. Thus, the image generation section 21 identifies the luminance-unevenness region. As a result, for example, as the binarized luminance-unevenness image (the binarized luminance-unevenness image data D23) illustrated in FIG. 9C, the luminance-unevenness region may be identified. Note that, in the binarized luminance-unevenness image illustrated in FIG. 9C, the luminance-unevenness region is illustrated by white, and other regions are illustrated by black (the image illustrated in FIG. 9C is the binarized image).

(2-5. Calculation of Luminance-Unevenness Evaluation Value El)

Subsequently, the parameter calculation section 22 calculates the luminance-unevenness evaluation value El in the following manner (steps S141 to S142 in FIG. 2).

First, the parameter calculation section 22 uses the various kinds of luminance-unevenness inspection images (the luminance-unevenness image data D21, the luminance edge image data D22, and the binarized luminance-unevenness image data D23) generated in the above manner, to calculate various kinds of parameters described below (step S141).

Specifically, the parameter calculation section 22 uses the luminance edge image (the luminance edge image data D22) to calculate a luminance edge area ratio Sle that is an area ratio of the luminance edge region with respect to the entire region of the inspection target (the entire display pixel region in the display screen).

Further, the parameter calculation section 22 uses the binarized luminance-unevenness image (the binarized luminance-unevenness image data D23) to calculate a luminance-unevenness area ratio Sl that is an area ratio of the luminance-unevenness region with respect to the entire region of the inspection target (the entire display pixel region in the display screen).

Furthermore, the parameter calculation section 22 uses the luminance-unevenness image (the luminance-unevenness image data D21) to calculate a maximum luminance difference ΔL*max (=Max|L*−L*ave|) that is a maximum value of an absolute value of a difference between the luminance (L*) in the entire luminance-unevenness region and the average luminance L*ave. For example, in the example of the luminance-unevenness image illustrated in FIG. 9A, the maximum luminance difference ΔL*max is exhibited in the image pickup pixel indicated by a symbol "x" in FIG. 9D.

Then, the parameter calculation section 22 weights and adds the luminance edge area ratio Sle, the luminance-unevenness area ratio Sl, and the maximum luminance difference ΔL*max that are thus calculated, to calculate the luminance-unevenness evaluation value El (step S142). Specifically, the parameter calculation section 22 may use, for example, the following expression (12) to calculate the luminance-unevenness evaluation value El. Note that, in the expression (12), each of constants (coefficients) k4, k5, and k6 represents a weighting coefficient, and c2 represents a predetermined constant (including 0).

$$El = k4 \times Sle + k5 \times Sl + k6 \times \Delta L^* \max + c2 \qquad (12)$$

(2-6. Calculation of Integrated Evaluation Value E and Unevenness Inspection Processing)

Next, the parameter calculation section 22 may use, for example, the following expression (13) to calculate the integrated evaluation value E for the unevenness inspection, based on the color-unevenness evaluation value Ec and the luminance-unevenness evaluation value El that are obtained in this way (step S151). Specifically, the parameter calculation section 22 weights and adds the color-unevenness evaluation value Ec and the luminance-unevenness evaluation value El to calculate the integrated evaluation value E. As a result, it becomes possible to perform inspection reflecting the weighting of the color-unevenness evaluation value Ec and the luminance-unevenness evaluation value El in the unevenness inspection described below. Incidentally, in the expression (13), each of constants (coefficients) A and B represents a weighting coefficient, and c3 represents a predetermined constant (including 0).

$$E = A \times Ec + B \times El + c3 \qquad (13)$$

Here, in the present embodiment, the parameter calculation section 22 calculates the integrated evaluation value E in consideration of unevenness visibility with respect to both of color and luminance. Specifically, each of the above-described weighting coefficients A and B is determined in consideration of the unevenness visibility with respect to both of color and luminance. In this way, since the integrated evaluation value E is calculated in consideration of the unevenness visibility with respect to both of color and luminance, objective unevenness inspection further matched with human sense is realized, as compared with the case where the unevenness inspection is performed without considering such visibility.

Subsequently, the inspection processing section 23 uses the integrated evaluation value E thus obtained, to perform unevenness inspection on the display screen of the display unit 4 that is an inspection target, and then generates the inspection result data Dout as a result of the inspection (step S152). Specifically, for example, the inspection processing section 23 determines that the degree of unevenness in the inspection target (one or both of the color-unevenness and the luminance-unevenness) is large, based on increase of the integrated evaluation value E. On the other hand, the inspection processing section 23 determines that the degree of unevenness in the inspection target is small, based on decrease of the integrated evaluation value E. Alternatively, when the integrated evaluation value E is equal to or greater than the predetermined threshold, the inspection processing section 23 determines that the inspection target is a defective, whereas when the integrated evaluation value E is smaller than the above-described threshold, the inspection processing section 23 determines that the inspection target is a confirming item. In this way, the unevenness inspection processing by the image processing apparatus 2 is ended.

Example 1

Here, FIG. 10 illustrates an example (Example 1) illustrating relationship (correlation) between the various kinds of evaluation values described above and the subjective evaluation value (the ME value). Specifically, FIG. 10A illustrates correlation between the color-unevenness evaluation value Ec and the subjective evaluation value (the ME value) according to the Example 1, FIG. 10B illustrates correlation between the luminance-unevenness evaluation value El and the subjective evaluation value (the ME value) according to the Example 1, and FIG. 10C illustrates correlation between the integrated evaluation value E and the subjective evaluation value (the ME value) according to the Example 1. Note that a determination coefficient IV in a linear line illustrated in these figures indicates that accuracy of the unevenness inspection becomes higher as the determination coefficient IV becomes a large value close to "1".

First, in an example illustrated in FIG. 10A, subjective evaluation was performed based on the evaluation result by magnitude estimation with respect to 25 men and women between the ages of 19 and 24 as examinees. Moreover, in this example, the color-unevenness evaluation value Ec was calculated when the weighting coefficient k1 with respect to the chroma edge area ratio Sce was 12.8, the weighting coefficient k2 with respect to the color-unevenness area ratio Sc was 4.0, and the weighting coefficient k3 with respect to the maximum chroma Cmax was 0.02. In this example, the determination coefficient R2 was 0.94, which exhibited extremely higher correlation.

On the other hand, an example illustrated in FIG. 10B was based on the evaluation result by the magnitude estimation under the condition similar to that in the case of FIG. 10A. Moreover, in this example, the luminance-unevenness evaluation value El was calculated when the weighting coefficient k4 with respect to the luminance edge area ratio Sle was 19.9, the weighting coefficient k5 with respect to the luminance-unevenness area ratio SI was 1.9, and the weighting coefficient k6 with respect to the maximum luminance difference L*max was 0.19. Also in this example, the determination coefficient R2 was 0.94, which exhibited extremely higher correlation.

On the other hand, an example illustrated in FIG. 10C was based on the evaluation result by the magnitude estimation under the condition similar to that in the case of FIG. 10A. Moreover, in this example, the integrated evaluation value E was calculated when the weighting coefficient A with respect to the color-unevenness evaluation value Ec was 0.63, and the weighting coefficient B with respect to the luminance-unevenness evaluation value El was 0.71. Also in this example, the determination coefficient R2 was 0.95, which exhibited extremely higher correlation.

Example 2

Also, FIG. 11A, FIG. 11B, and FIG. 12 each illustrate an example (Example 2) illustrating comparison of difference of the edge region at the time when the edge region (the luminance edge region) was identified by comparison between the predetermined edge threshold and one of the above-described variation per unit length and the above-described variation per unit visual angle.

Specifically, FIG. 11A illustrates relationship between the size [inch] of the display screen as the inspection target and appropriate visual distance [mm] and the visual angle [ ] per 1 mm of the observer in each size (8 inches, 40 inches, and 80 inches) according to the Example 2. Also, FIG. 11B schematically illustrates relationship between each appropriate visual distance and the visual angle per 1 mm illustrated in FIG. 11A.

On the other hand, FIG. 12 illustrates comparison of the luminance edge image (the luminance edge image data D22) when the above-described (dL*/mm)=0.5 was used as the luminance edge threshold and the luminance edge image when the above-described (dL*/arcmin)=0.218 was used as the luminance edge threshold, for each appropriate visual distance (each size of the display screen) illustrated in FIG. 11A and FIG. 11B. Specifically, FIG. 12 illustrates comparison of difference of the edge region identified when the luminance edge region was defined with use of the luminance variation (the luminance edge intensity) per unit length on the display screen and when the luminance edge region was defined with use of the luminance variation per unit visual angle.

It was found from the Example 2 illustrated in FIG. 11A, FIG. 11B, and FIG. 12 that the following effects are obtainable when the luminance edge region is defined with use of the luminance variation per unit visual angle (in the case where the luminance edge threshold (dL*/arcmin) is 0.218). Specifically, unlike the case where the luminance edge region is defined with use of the luminance variation per unit length on the display screen (in the case where the luminance edge threshold (dL*/mm) is 0.5), it becomes possible to identify a certain luminance edge region irrespective of the size of the display screen (the appropriate visual distance of the observer). Accordingly, it is possible to improve accuracy of the unevenness inspection.

Note that, in the Example 2, the difference of the edge region when the luminance edge region is identified has been illustrated. However, the same applies to the difference of the edge region when the chroma edge region is identified. In other words, when the chroma edge region is defined with use of the chroma variation per unit visual angle, it is possible to identify a certain chroma edge region irrespective of the size of the display screen (the appropriate visual angle of the observer), unlike the case where the chroma edger region is defined with use of the chroma variation per unit length on the display screen.

Example 3

FIG. 13 illustrates comparison of the chroma edge image (the chroma edge image data D12) and the binarized color-unevenness images (the binarized color-unevenness image data D13) according to a comparative example and Example 3. Moreover, FIG. 14 illustrates comparison of the luminance edge image (the luminance edge image data D22) and the binarized luminance-unevenness image (the binarized luminance-unevenness image data D23) according to the comparative example and the Example 3.

Here, the Example 3 corresponded to an example in a case where the above-described filter processing was performed after the image separation processing in the present embodiment was performed, and the comparative example corresponded to an example in a case where the above-described filter processing was performed without performing the image separation processing in the present embodiment. Further, an image without color-unevenness was used as the inspection target in FIG. 13, whereas an image without luminance-unevenness was used as the inspection target in FIG. 14.

In the example illustrated in FIG. 13, although the inspection target was the image without color-unevenness, the above-described false color-unevenness component occurred in both of the chroma edge image and the binarized color-unevenness image in the comparative example, (the determination result: cross). Therefore, in the comparative example, it was difficult to perform accurate color-unevenness inspection. In contrast, in the Example 3, occurrence of such false color-unevenness component was avoided (the determination result: circle). In other words, performing the above-described filter processing after the image separation processing in the present embodiment makes it possible to perform more accurate color-unevenness inspection without including false color-unevenness information in the color space conversion.

Moreover, in the example illustrated in FIG. 14, although the inspection target was the image without luminance-unevenness, the above-described false luminance-unevenness component occurred in the binarized luminance-unevenness image in the comparative example (the determination result: cross). Therefore, it was difficult to perform accurate luminance-unevenness inspection in the comparative example. In contrast, in the Example 3, occurrence of such false luminance-unevenness component was avoided (the determination result: circle). In other words, performing the above-described filter processing after the image separation processing in the present embodiment makes it possible to perform more accurate luminance-unevenness inspection without including the false luminance-unevenness information in the color space conversion.

As described above, in the present embodiment, at the time of calculating the integrated evaluation value E with use of both of the color-unevenness inspection images (the various kinds of image data D11 to D13) and the luminance-unevenness inspection images (the various kinds of image data D21 to D23), the unevenness visibility with respect to both of color and luminance is considered. Accordingly, it is possible to realize objective unevenness inspection further matched with human sense (integrated unevenness inspection including the color-unevenness inspection and the luminance-unevenness inspection). Moreover, at the time of generating such color-unevenness inspection images and such luminance-unevenness inspection images, the filter processing taking account of the visual spatial frequency characteristics is performed after the image separation processing for separating the color component and the luminance component is performed. Therefore, occurrence of the false color-unevenness component and the false luminance-unevenness component is avoided, which makes it possible to realize more accurate unevenness inspection. Consequently, it becomes possible to perform appropriate unevenness inspection.

Further, at the time of generating the color-unevenness inspection images, the chroma C is calculated while performing the correction processing (the gain correction processing to a*) taking account of difference of the color-unevenness visibility depending on colors for each of the image pickup pixels of the picked-up image. Therefore, it is possible to realize the objective unevenness inspection further matched with human sense, and to perform further appropriate unevenness inspection.

Further, since the objective unevenness inspection further matched with human sense is realized, it is possible to improve efficiency in development and design by using the subjective unevenness inspection in quality assessment in development and design.

Moreover, introducing the unevenness inspection in the present embodiment in, for example, inspection process for mass production makes it possible to perform unevenness inspection stably and rapidly. This makes it possible to improve efficiency of assessment process and to improve stability of quality of the product.

In addition, since the edge region (the luminance edge region and the chroma edge region) is defined with use of variation (the luminance variation and the chroma variation) per unit visual angle, it becomes possible to identify minute edge region on the display screen as described below. Specifically, first, for example, as illustrated in FIG. 15, for example, when the edge region is identified with use of luminance difference, chroma difference, or the like between the pixels distanced by a pitch corresponding to a visual angle of 0.1 [rad] or larger, the minute edge region is not identified, for example, in the large screen size of 40 [inches] or 80 [inches]. This is because, as illustrated in FIG. 15, the pitch on the display screen corresponding to the visual angle of 0.1 [rad] becomes several hundred [mm] In contrast, in the case where the edge region is defined with use of the variation per unit visual angle, for example, when the unit visual angle is assumed to be 1 ['] as illustrated in FIG. 15, the pitch on the display screen corresponding to the unit visual angle may be suppressed to be smaller than 1 [mm] even if the size of the display screen is large. Accordingly, for example, in consideration of the case where the size of the display screen is large or the case where the high definition mobile display is observed from an appropriate visual distance, it is possible to identify the minute edge region. This makes it possible to improve accuracy in the unevenness inspection.

Note that the edge region may be defined by varying the threshold (the edge threshold) of the variation (the luminance variation and the chroma variation) per unit length on the display screen based on the visual distance, instead of defining the edge region with use of the variation per unit visual angle as described above. Specifically, for example, the luminance edge threshold and the chroma edge threshold may be defined with use of the following expressions (14) and (15). Incidentally, in these expressions, D represents the visual distance [mm], Lth (=0.5) represents the luminance edge threshold per unit length when the visual distance D is 1500 [mm], and Cth (=2.0) represents the chroma edge threshold per unit length when the visual distance D is 1500 [mm] In this way, also when the edge region is defined by varying the edge threshold per unit length based on the visual distance, it is possible to identify the minute edge region and to improve accuracy in the unevenness inspection, similarly to the case where the edge region is defined with use of the variation per unit visual angle.

Luminance Edge Threshold: $(dL^*/dx)=Lth\times(1500/D)$ (14)

Chroma Edge Threshold: $(dC^*/dx)=Cth\times(1500/D)$ (15)

<Modifications>

Subsequently, modifications (modifications 1 and 2) of the above-described embodiment are described. The modifications 1 and 2 correspond to examples (clouded configuration examples) in which at least a part of the functions of the image processing section 2 described in the embodiment (the functions of the image generation section 21, the parameter calculation section 22, and the inspection processing section 22) is provided in a server, and network communication is performed. Note that like numerals are used to designate substantially like components in the embodiment, and the description thereof is appropriately omitted.

[Modification 1]
(Configuration)

FIG. 16 schematically illustrates an outline configuration example of an unevenness inspection system (an unevenness inspection system 1A) according to the modification 1, together with inspection targets 4A to 4D. The unevenness inspection system 1A in the present modification includes a server 2A, a plurality of pairs of (four pairs in this example) image pickup apparatuses (image pickup sections) 3A to 3D and control apparatuses 5A to 5D and a management apparatus (a management section) 6 that are connected with the server 2A through wired or wireless network NW.

Further, the four pairs of image pickup apparatuses 3A to 3D and control apparatuses 5A to 5D are disposed for each of steps (manufacturing steps) A to D in manufacture of the inspection targets 4A to 4D, and the unevenness inspection described in the above-described embodiment is performed individually in each of the steps A to D as described later. Here, the step A corresponds to a step of manufacturing the inspection target 4A (a backlight), and the step B corresponds to a step of manufacturing the inspection target 4B (a liquid crystal panel). Also, the step C corresponds to a step of manufacturing the inspection target 4C (a panel module), and the step D corresponds to a step of manufacturing the inspection target 4D (a liquid crystal display unit that is a final product).

Incidentally, the unevenness inspection method and the unevenness inspection program according to the present modification are embodied in the unevenness inspection system 1A of the present modification. Therefore, the unevenness inspection method and the unevenness inspection program are described together.

The server 2A includes the image generation section 21, the parameter calculation section 22, and the inspection processing section 23. In other words, the image generation section 21, the parameter calculation section 22, and the inspection processing section 23 are all provided in the server 2A. For example, the server 2A may have a function of identifying individual identification symbols of the control apparatuses 5A to 5D, individual identification symbols of the image pickup apparatuses 3A to 3D, or an individual identification symbol of a user. Moreover, for example, the server 2A may have a function of performing storage of transferred picked-up image data Din and performing the unevenness inspection processing to store the inspection result data Dout in itself or to transfer the inspection result data Dout to the control apparatuses 5A to 5D. Such a server 2A may be configured of, for example, an image processing data storage apparatus that is clustered at high speed on a large scale.

The control apparatuses 5A to 5D are each connected to the server 2A through the above-described network NW, and have functions of controlling operation of the image pickup apparatus 3A to 3D, respectively, controlling data transmission and reception, and displaying the unevenness inspection result. Specifically, the control apparatuses 5A to 5D may transmit the picked-up image data Din obtained from the image pickup apparatuses 3A to 3D, respectively, to the server 2A through the network NW, and may receive the inspection result data Dout that is supplied from the server 2A to display the inspection result data Dout on its display section. In addition, at this time, for example, the control apparatuses 5A to 5D may each compress and transfer the picked-up image data Din according to the needs of equipment for circuit capacity of the network NW and the like. In this way, in the present modification, the image pickup apparatuses 3A to 3D are network-connected to the server 2A indirectly (through the control apparatuses 5A to 5D, respectively). Note that the control apparatuses 5A to 5D may be each configured using, for example, a personal computer (PC).

The management apparatus 6 has a function of collectively managing results of the unevenness inspection (the inspection result data Dout) performed at each of the above-described steps 4A to 4D, as will be described later.

(Action and Effects)

Here, for example, when the unevenness inspection is performed individually at each of the steps A to D with use of the image processing apparatus 2 that is configured of a PC or the like described in the above-described embodiment, the following issues may occur.

First, the first issue is as follows. Specifically, for example, when the image pickup apparatus 3A used at the step A is of XYZ filter type and the number of data points is one million pixels, data stream of one million dots is obtained as three pieces of picked-up image data Din. This corresponds to data amount of about 40 MB as a normal text file. When the series of unevenness inspection processing described in the above-described embodiment is performed based on such picked-up image data Din, the data amount doubles only by the image separation processing, and a memory amount secured for working at one step increases about 10 times.

Further, even if the color-unevenness inspection images (the various kinds of image data D11 to D13) and the luminance-unevenness inspection images (the various kinds of image data D21 to D23) are stored as bit map data for latter management, it is necessary to store six pieces of one million pixel data at one inspection step, and it is thus necessary to secure the memory amount of about 6 MB. In addition, if these images are stored as numerical sequence data, it is necessary to secure the memory amount of about 100 MB. In this way, when management maintaining traceability is performed, it is necessary to secure a storage region close to 150 MB at one step for one inspection target and a working memory sufficient for successive data development of 400 MB. For example, when one million display units are manufactured in one year, a manufacturing tact for one unit becomes about 30 seconds, and thus storage capacity of about 430 GB is necessary per day.

Performing processing and storage of such vast amount of data at each step demands a high cost, and the data amount is further increased as the step proceeds to the step B, the step C, and the step D. Therefore, it is not easy to secure traceability even when defect determination occurs in the inspection.

Moreover, the second issue is as follows. Specifically, for example, in the recent method of manufacturing the display unit, manufacturing the final product at one place is rare. At present, the manufacturing plant is changed for each assembly, and further, cross-border transportation is performed. However, inspection system in shipping inspection and arrival inspection in the middle may not be adequate, and it is difficult to perform management of occurrence of defect such as unevenness in practice.

Accordingly, in the unevenness inspection system 1A in the present modification, as described above, the functions of the image processing apparatus 2 (the image generation section 21, the parameter calculation section 22, and the inspection processing section 22) are provided in the server 2A, and the image pickup apparatuses 3A to 3D and the control apparatuses 5A to 5D provided at the steps A to D, respectively, are network-connected with the server 2A. As a result, the expensive image processing apparatus 2 capable of performing high-speed computing may be replaced with an inexpensive PC or the like having a function of, for example, data compression and data transfer, which may result in reduction in production cost. In other words, at each of the steps A to D, acquisition of the picked-up image Din by the image pickup apparatus 3A to 3D and display of the inspection result data Dout are only performed, which reduces the manufacturing cost and avoids oppression of manufacturing tact by the inspection. Consequently, it becomes possible to realize more appropriate unevenness inspection at high speed with low cost, and to perform quality management easily.

Moreover, if the inspection information at each of the steps A to D are uniformly managed, traceability of defect determined at the inspection step is secured, which makes it possible to promptly perform investigation of the cause of the defect and development of countermeasures. For example, if defect occurs in the inspection at the step D, it becomes possible to determine whether the defect is caused by accumulated factors or the defect suddenly occurs only at the step D by reference to connected data at other steps. Accordingly, it becomes possible to rapidly determine the cause of the defect, and to minimize manufacturing defects. Moreover, when the defect is caused by accumulated factors, it is possible to promptly provide feedback to the design. This makes it possible to prevent accumulation of defects. Further, performing the same inspection at shipping and arriving makes it easy to found defect by transportation. Thus, entire quality management becomes easy. In addition, since the operation for calculating the evaluation results are uniformly managed, it is possible to prevent operational mistake, intentional falsification, etc. at each step, which makes it easy to perform quality management. In this way, the quality management becomes easy, and quality preservation of the product to be provided to general consumers, furthermore, quality improvement and inventory management adjustment are also performed easily.

Further, for example, when a server manager on the network NW charges a user for management instead of reducible cost of the image processing unit 2 and performs management, it becomes possible for the user to receive the benefits of computing at a constant high-speed and management and storage of the data. Accordingly, when the inspection at shipping and arriving is performed utilizing the inexpensive inspection cost, it becomes possible to manage the defects and the like occurred in transportation. Note that examples of the charging method at this time may include charging to a user having a user identification symbol, for example, depending on the size of the image, the size of the image data, process time, or a combination thereof.

Note that, in the present modification, the case where the image generation section 21, the parameter calculation section 22, and the inspection processing section 23 are all provided in the server 2A has been described as an example, however the configuration is not limited thereto. Alternatively, one or more of the image generation section 21, the parameter calculation section 22, and the inspection processing section 23 may be provided in the single server 2A. Also, the unevenness inspection system 1A may include not the plurality of image pickup apparatuses (image pickup sections) but only one image pickup apparatus.

[Modification 2]

FIG. 17 schematically illustrates an outline configuration example of an unevenness inspection system (an unevenness inspection system 1B) according to the modification 2, together with the inspection targets 4A to 4D. The unevenness inspection system 1B of the present modification includes the server 2A, and the plurality of (four in this example) image pickup apparatuses 3A to 3D and the management apparatus 6 that are connected with the server 2A through the wired or wireless network NW. In other words, the unevenness inspection system 1B corresponds to a system configured by omitting (not providing) the control apparatuses 5A to 5D at the respective steps A to D from the unevenness inspection system 1A of the modification 1, and other configurations of the unevenness inspection system 1B are basically similar to those of the unevenness inspection system 1A of the modification 1. Note that the unevenness inspection method and the unevenness inspection program according to the present modification are embodied in the unevenness inspection system 1A of the present modification. Thus, the unevenness inspection method and the unevenness inspection program according to the present modification will be described together below.

In the present modification, each of the image pickup apparatuses 3A to 3D is connected to the serer 2A through the network NW, and has a function of performing data transmission and data reception. Specifically, each of the image pickup apparatuses 3A to 3D may transmit the obtained picked-up image data Din to the server 2A through the network NW, and may receive the inspection result data Dout supplied from the server 2A. Further, at this time, for example, each of the image pickup apparatuses 3A to 3D may compress and transfer the picked-up image data Din according to the needs of equipment for circuit capacity of the network NW and the like. In this way, in the present modification, each of the image pickup apparatuses 3A to 3D is network-connected with the server 2A directly (without the control apparatuses 5A to 5D).

Also in the present modification having such a configuration, it is possible to basically obtain effects similar to those of the above-described modification 1 by the similar functions.

Moreover, in the present modification in particular, the control apparatuses 5A to 5D are unnecessary. Therefore, it is possible to further reduce cost at each of the steps.

Incidentally, also in the present modification, one or more of the image generation section 21, the parameter calculation section 22, and the inspection processing section 22 may be provided in the single server 2A. Moreover, the unevenness inspection system 1B may include not the plurality of image pickup apparatuses (image pickup sections) but only one image pickup apparatus.

<Other Modifications>

Hereinbefore, although the technology of the disclosure has been described with referring to the embodiment and the modifications, the technology is not limited to the embodiment and the like, and various modifications may be made.

For example, in the above-described embodiment and the like, the case where the three parameters of the chroma edge area ratio Sce, the color-unevenness area ratio Sc, and the maximum chroma Cmax are used as the color-unevenness evaluation value Ec has been described. However, other parameters may be used in addition thereto (or in place thereof). In addition, one or more of the three parameters may be used as the color-unevenness evaluation value Ec. Incidentally, out of the three parameters, in particular, at least two parameters of the chroma edge area ratio Sce and the color-unevenness area ratio Sc may be desirably used. This is because these two parameters contribute to the color-unevenness evaluation value Ec relatively largely since human being tends to give weight to spatial extent in determination of the degree of color-unevenness.

Also, in the above-described embodiment and the like, the case where the three parameters of the luminance edge area ratio Sle, the luminance-unevenness area ratio Sl, and the maximum luminance difference $\Delta L^*max$ are used as the luminance-unevenness evaluation value El has been described. However, other parameters may be used in addition thereto (or in place thereof). In addition, one or more of the three parameters may be used as the luminance-unevenness evaluation value El. Incidentally, out of the three parameters, in particular, at least two parameters of the luminance-edge area ratio Sle and the luminance-unevenness area ratio Sl may be desirably used. This is because these two parameters contribute to the luminance-unevenness evaluation value El relatively largely since human being tends to give weight to spatial extent in determination of the degree of luminance-unevenness.

Further, in the above-described embodiment and the like, the examples of the color-unevenness inspection image and the luminance-unevenness inspection image have been specifically described. However, the color-unevenness inspection image and the luminance-unevenness inspection image are not limited to those described in the above-described embodiment.

In addition, in the above-described embodiment and the like, the case where the chroma C is calculated while the correction processing (the gain correction processing) taking account of difference of the color-unevenness visibility depending on colors is performed in generation of the color-unevenness inspection images has been described. However, such gain correction processing may not be performed depending on a case.

Moreover, in the above-described embodiment and the like, the case where the inspection target of the unevenness inspection is the display screen of the display unit performing color picture display has been described. However, the inspection target of the technology may be other than the display unit (for example, an illumination unit (such as a backlight)).

Furthermore, in the above-described embodiment and the like, the case where the image pickup apparatus and the image processing apparatus are separated from each other in the unevenness inspection system has been described. However, these apparatuses may be provided in the same apparatus.

In addition, the series of processes (the respective functions of the image generation section, the calculation section, the inspection section, the management section, and the like) described in the above-described embodiment and the like may be executed by hardware (circuits) or may be executed by software (programs). In the case where the series of processes is executed by software, the software is configured of a program group causing a computer (PC, a microcomputer in the server, or the like) to execute each of the above-described functions. For example, each program may be incorporated in the above-described computer in advance or may be installed from any network or a recording medium to the above-described computer and used.

Note that the technology may be configured as follows.

[1] An unevenness inspection system including:

an image pickup section configured to acquire a picked-up image of an inspection target;

an image generation section configured to generate a color-unevenness inspection image and a luminance-unevenness inspection image, based on the picked-up image;

a calculation section configured to use both of the color-unevenness inspection image and the luminance-unevenness inspection image to calculate an evaluation parameter; and an inspection section configured to use the calculated evaluation parameter to perform unevenness inspection, wherein the image generation section performs image separation processing to separate a color component and a luminance component on the picked-up image, to generate a color-component image and a luminance-component image, and individually performs filter processing taking account of visual spatial frequency characteristics on the color-component image and the luminance-component image to respectively generate the color-unevenness inspection image and the luminance-unevenness inspection image, based on the filter-processed color-component image and the filter-processed luminance-component image, and the calculation section calculates the evaluation parameter in consideration of unevenness visibility with respect to both of color and luminance.

[2] The unevenness inspection system according to [1], wherein the calculation section uses the color-unevenness inspection image to calculate a color-unevenness evaluation parameter and uses the luminance-unevenness inspection image to calculate a luminance-unevenness evaluation parameter, and weights and adds the color-unevenness evaluation parameter and the luminance-unevenness evaluation parameter to calculate an integrated evaluation parameter as the evaluation parameter.

[3] The unevenness inspection system according to [2], wherein the integrated evaluation parameter E is represented by following expression (1), and weighting coefficients A and B are determined in consideration of the unevenness visibility, $$E = A \times Ec + B \times El \quad (1)$$

where Ec represents the color-unevenness evaluation parameter, El represents the luminance-unevenness evaluation parameter, and A and B represent the weighting coefficients.

[4] The unevenness inspection system according to [2] or [3], wherein
the inspection section determines that a degree of unevenness in the inspection target is large, based on increase of the integrated evaluation parameter, and determines that the degree of unevenness in the inspection target is small, based on decrease of the integrated evaluation parameter.

[5] The unevenness inspection system according to any one of [1] to [4], wherein
the image generation section performs correction processing taking account of difference of color-unevenness visibility depending on colors, on the filter-processed color-component image, and then generates the color-unevenness inspection image.

[6] The unevenness inspection system according to [5], wherein
the image generation section calculates chroma after performing the correction processing, in each unit region of the filter-processed color-component image, and uses the calculated chroma to generate the color-unevenness inspection image.

[7] The unevenness inspection system according to [6], wherein
the image generation section calculates values (a*, b*) in CIELAB color space in each unit region of the filter-processed color-component image, and performs gain correction processing that is represented by following expression (2) as the correction processing, on the calculated value a*, and then calculates chroma C with use of following expression (3), $$a^{*\prime} = (\alpha \times a^*)(\text{for } a^* > 0 : \text{gain } \alpha > 1, \text{for } a^* \le 0 : \text{gain } \alpha = 1) \quad (2)$$

$$C = \{(a^{*\prime})^2 + (b^*)^2\}^{1/2} \quad (3)$$

[8] The unevenness inspection system according to any one of [2] to [7], wherein
as the color-unevenness evaluation parameter, at least a chroma edge area ratio that is an area ratio of a chroma edge region to entire region of the inspection target and a color-unevenness area ratio that is an area ratio of a color-unevenness region to the entire region of the inspection target are used.

[9] The unevenness inspection system according to [8], wherein
as the color-unevenness evaluation parameter, the chroma edge area ratio, the color-unevenness area ratio, and a maximum chroma in the entire color-unevenness region are used.

[10] The unevenness inspection system according to [9], wherein
the calculation section uses the color-unevenness inspection image to calculate the chroma edge area ratio, the color-unevenness area ratio, and the maximum chroma, and weights and adds the chroma edge area ratio, the color-unevenness area ratio, and the maximum chroma to calculate the color-unevenness evaluation parameter.

[11] The unevenness inspection system according to any one of [2] to [10], wherein
as the luminance-unevenness evaluation parameter, at least a luminance edge area ratio that is an area ratio of a luminance edge region to entire region of the inspection target and a luminance-unevenness area ratio that is an area ratio of a luminance-unevenness region to the entire region of the inspection target are used.

[12] The unevenness inspection system according to [11], wherein
as the luminance-unevenness evaluation parameter, the luminance edge area ratio, the luminance-unevenness area ratio, and a maximum luminance difference are used, the maximum luminance difference being a maximum value of an absolute value of a difference between luminance in the entire luminance-unevenness region and average luminance of a white image.

[13] The unevenness inspection system according to [12], wherein
the calculation section uses the luminance-unevenness inspection image to calculate the luminance edge area ratio, the luminance-unevenness area ratio, and the maximum luminance difference, and weights and adds the luminance edge area ratio, the luminance-unevenness area ratio, and the maximum luminance difference to calculate the luminance-unevenness evaluation parameter.

[14] The unevenness inspection system according to any one of [1] to [13], wherein
one or more of the image generation section, the calculation section, and the inspection section are provided in a single server, and
the image pickup section is provided in each of one or a plurality of image pickup apparatuses that are directly or indirectly connected to the server through network.

[15] The unevenness inspection system according to [14], wherein
the image pickup apparatus is provided for every plurality of steps in manufacturing the inspection target, and
unevenness inspection by the inspection section is performed individually for every plurality of steps.

[16] The unevenness inspection system according to [15], further including
a management section connected to the network and configured to collectively manage results of the unevenness inspection performed for every plurality of steps.

[17] The unevenness inspection system according to any one of [14] to [16], wherein
the image generation section, the calculation section, and the inspection section are provided in the server, and the image pickup section is provided in each of the one or the plurality of image pickup apparatuses, and
the picked-up image is supplied from the image pickup apparatus to the server through the network, and result data of the unevenness inspection is supplied from the server to the image pickup apparatus through the network.

[18] The unevenness inspection system according to any one of [1] to [17], wherein
the inspection target is a display screen of a display unit performing color picture display.

[19] An unevenness inspection method including:
a step of acquiring a picked-up image of an inspection target;
a generation step of generating a color-unevenness inspection image and a luminance-unevenness inspection image, based on the picked-up image;
a calculation step of using both of the color-unevenness inspection image and the luminance-unevenness inspection image to calculate an evaluation parameter; and
an inspection step of using the calculated evaluation parameter to perform unevenness inspection, wherein
in the generation step, image separation processing to separate a color component and a luminance component is performed on the picked-up image to generate a color-component image and a luminance-component image, and filter processing taking account of visual spatial frequency characteristics is individually performed on the color-component image and the luminance-component image to respectively generate the color-unevenness inspection image and the luminance-unevenness inspection image, based on the filter-processed color-component image and the filter-processed unevenness-component image, and in the calculation step, the evaluation parameter is calculated in consideration of unevenness visibility with respect to both of color and luminance.

[20] An unevenness inspection program causing a computer to execute:

a step of acquiring a picked-up image of an inspection target;

a generation step of generating a color-unevenness inspection image and a luminance-unevenness inspection image, based on the picked-up image;

a calculation step of using both of the color-unevenness inspection image and the luminance-unevenness inspection image to calculate an evaluation parameter; and an inspection step of using the calculated evaluation parameter to perform unevenness inspection, wherein in the generation step, image separation processing to separate a color component and a luminance component is performed on the picked-up image to generate a color-component image and a luminance-component image, and filter processing taking account of visual spatial frequency characteristics is individually performed on the color-component image and the luminance-component image to respectively generate the color-unevenness inspection image and the luminance-unevenness inspection image, based on the filter-processed color-component image and the filter-processed luminance-component image, and in the calculation step, the evaluation parameter is calculated in consideration of unevenness visibility with respect to both of color and luminance.

This application is based upon and claims the benefit of priority of the Japanese Patent Application No. 2013-41573 filed in the Japan Patent Office on Mar. 4, 2013, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

What is claimed is:

1. An unevenness inspection system comprising:
circuitry configured to:
acquire a picked-up image of an inspection target;
separate a color component and a luminance component on the picked-up image;
generate a color-component image and a luminance-component image based on the separated color component and luminance component;
individually filter process taking account of visual spatial frequency characteristics on the color-component image and the luminance-component image;
generate a color-unevenness inspection image and a luminance-unevenness inspection image, based on the filter-processed color-component image and the filter-processed luminance-component image;
calculate, based on the color-unevenness inspection image, at least a color-unevenness area ratio that is an area ratio of a color-unevenness region to the entire region of the inspection target as a color-unevenness evaluation parameter;

calculate a luminance-unevenness evaluation parameter based on the luminance-unevenness inspection image;
integrate the color-unevenness evaluation parameter and the luminance-unevenness evaluation parameter together to generate an evaluation parameter; and
use the evaluation parameter to perform unevenness inspection in a manufacturing process of the inspection target independently from a capability of an inspector.

2. The unevenness inspection system according to claim 1, wherein
the circuitry is further configured to use the color-unevenness inspection image to calculate a color-unevenness evaluation parameter and use the luminance-unevenness inspection image to calculate a luminance-unevenness evaluation parameter, and weights and add the color-unevenness evaluation parameter and the luminance-unevenness evaluation parameter to calculate an integrated evaluation parameter E as the evaluation parameter.

3. The unevenness inspection system according to claim 2, wherein
the integrated evaluation parameter E is represented by following expression (1), and weighting coefficients A and B are determined in consideration of an unevenness visibility, $$E = A \times Ec + B \times El \quad (1)$$

where Ec represents the color-unevenness evaluation parameter, El represents the luminance-unevenness evaluation parameter, and A and B represent the weighting coefficients.

4. The unevenness inspection system according to claim 2, wherein
the circuitry is further configured to determine that a degree of unevenness in the inspection target is large, based on increase of the integrated evaluation parameter, and determine that the degree of unevenness in the inspection target is small, based on decrease of the integrated evaluation parameter.

5. The unevenness inspection system according to claim 1, wherein
the circuitry is further configured to perform correction processing taking account of difference of color-unevenness visibility depending on colors, on the filter-processed color-component image, and then generate the color-unevenness inspection image.

6. The unevenness inspection system according to claim 5, wherein
the circuitry is further configured to calculate chroma after performing the correction processing, in each unit region of the filter-processed color-component image, and use the calculated chroma to generate the color-unevenness inspection image.

7. The unevenness inspection system according to claim 6, wherein
the circuitry is further configured to calculate values ($a^*$, $b^*$) in CIELAB color space in each unit region of the filter-processed color-component image, and perform gain correction processing that is represented by following expression (2) as the correction processing, on the calculated value $a^*$, and then calculates chroma C with use of following expression (3), $$a^{*\prime} = (\alpha \times a^*) \text{ (for } a^* > 0 \text{: gain } \alpha > 1, \text{ [or } a^* \leq 0 \text{: gain } \alpha = 1) \quad (2)$$

$$C = \{(a^{*\prime})^2 + (b^*)^2\}^{1/2} \quad (3)$$

8. The unevenness inspection system according to claim 2, wherein as the color-unevenness evaluation parameter, at least a chroma edge area ratio that is an area ratio of a chroma edge region to entire region of the inspection target and the color-unevenness area ratio that is the area ratio of the color-unevenness region to the entire region of the inspection target are used.

9. The unevenness inspection system according to claim 8, wherein
as the color-unevenness evaluation parameter, the chroma edge area ratio, the color-unevenness area ratio, and a maximum chroma in the entire color-unevenness region are used.

10. The unevenness inspection system according to claim 9, wherein
the circuitry is further configured to use the color-unevenness inspection image to calculate the chroma edge area ratio, the color-unevenness area ratio, and the maximum chroma, and weights and add the chroma edge area ratio, the color-unevenness area ratio, and the maximum chroma to calculate the color-unevenness evaluation parameter.

11. The unevenness inspection system according to claim 2, wherein
as the luminance-unevenness evaluation parameter, at least a luminance edge area ratio that is an area ratio of a luminance edge region to entire region of the inspection target and a luminance-unevenness area ratio that is an area ratio of a luminance-unevenness region to the entire region of the inspection target are used.

12. The unevenness inspection system according to claim 11, wherein
as the luminance-unevenness evaluation parameter, the luminance edge area ratio, the luminance-unevenness area ratio, and a maximum luminance difference are used, the maximum luminance difference being a maximum value of an absolute value of a difference between luminance in the entire luminance-unevenness region and average luminance of a white image.

13. The unevenness inspection system according to claim 12, wherein
the circuitry is further configured to use the luminance-unevenness inspection image to calculate the luminance edge area ratio, the luminance-unevenness area ratio, and the maximum luminance difference, and weights and add the luminance edge area ratio, the luminance-unevenness area ratio, and the maximum luminance difference to calculate the luminance-unevenness evaluation parameter.

14. The unevenness inspection system according to claim 1, wherein
a first circuit of the circuitry is provided in a single server, and
a second circuit of the circuitry is provided in each of one or a plurality of image pickup apparatuses that are directly or indirectly connected to the server through network.

15. The unevenness inspection system according to claim 14, wherein
an image pickup apparatus is provided for every plurality of steps in manufacturing the inspection target, and unevenness inspection is performed individually for every plurality of steps.

16. The unevenness inspection system according to claim 15, wherein the circuitry is further configured to collectively manage results of the unevenness inspection performed for every plurality of steps.

17. The unevenness inspection system according to claim 14, wherein
the first circuit is provided in the server, and the second circuit is provided in each of the one or the plurality of image pickup apparatuses, and
the picked-up image is supplied from the image pickup apparatus to the server through the network, and result data of the unevenness inspection is supplied from the server to the image pickup apparatus through the network.

18. The unevenness inspection system according to claim 1, wherein
the inspection target is a display screen of a display performing color picture display.

19. An unevenness inspection method comprising:
acquiring a picked-up image of an inspection target;
separating a color component and a luminance component on the picked-up image;
generating a color-component image and a luminance-component image based on the separated color component and luminance component;
individually filter processing taking account of visual spatial frequency characteristics on the color-component image and the luminance-component image;
generating a color-unevenness inspection image and a luminance-unevenness inspection image, based on the filter-processed color-component image and the filter-processed luminance-component image;
calculating, based on the color-unevenness inspection image, at least a color-unevenness area ratio that is an area ratio of a color-unevenness region to the entire region of the inspection target as a color-unevenness evaluation parameter;
calculating a luminance-unevenness evaluation parameter based on the luminance-unevenness inspection image;
integrating the color-unevenness evaluation parameter and the luminance-unevenness evaluation parameter together to generate an evaluation parameter; and
using the evaluation parameter to perform unevenness inspection in a manufacturing process of the inspection target independently from a capability of an inspector.

20. A non-transitory computer readable medium storing an unevenness inspection program thereon that, when executed by a computer, causes the computer to perform a method comprising:
acquiring a picked-up image of an inspection target;
separating a color component and a luminance component on the picked-up image;
generating a color-component image and a luminance-component image based on the separated color component and luminance component;
individually filter processing taking account of visual spatial frequency characteristics on the color-component image and the luminance-component image;
generating a color-unevenness inspection image and a luminance-unevenness inspection image, based on the filter-processed color-component image and the filter-processed luminance-component image;
calculating, based on the color-unevenness inspection image, at least a color-unevenness area ratio that is an area ratio of a color-unevenness region to the entire region of the inspection target as a color-unevenness evaluation parameter;
calculating a luminance-unevenness evaluation parameter based on the luminance-unevenness inspection image;

integrating the color-unevenness evaluation parameter and the luminance-unevenness evaluation parameter together to generate an evaluation parameter; and using the evaluation parameter to perform unevenness inspection in a manufacturing process of the inspection target independently from a capability of an inspector.

21. An unevenness inspection system comprising:

circuitry configured to:

acquire a picked-up image of an inspection target;

convert a signal of the picked-up image into a signal formed of tristimulus values $X_i$, $Y_i$, and $Z_i$;

separate a color-component image and a luminance-component image on the picked-up image by (i) removing luminance-distribution information from the signal ($X_i$, $Y_i$, $Z_i$) while maintaining color distribution information to generate the color-component image formed of a signal ($X_C$, $Y_C$, $Z_C$), $X_C$ and $Z_C$ being calculated by the following expressions: $500\times[f(X_i/X_n)-f(Y_i/Y_n)]=500\times[f(X_C/X_n)-f(Y_C/Y_n)]$ and $200\times[f(Y_i/Y_n)-f(Z_i/Z_n)]=200\times[f(Y_C/Y_n)-f(Z_C/Z_n)]$; and (ii) removing color-distribution information from the signal ($X_i$, $Y_i$, $Z_i$) while maintaining luminance distribution information to generate the luminance-component image formed of a signal ($X_L$, $Y_L$, $Z_L$), $X_L$ and $Z_L$ being calculated by the following expressions: $500\times[f(X_L/X_n)-f(Y_L/Y_n)]=0$ and $200\times[f(Y_L/Y_n)-f(Z_L/Z_n)]=0$;

individually filter process taking account of visual spatial frequency characteristics on the color-component image and the luminance-component image;

generate a color-unevenness inspection image and a luminance-unevenness inspection image, based on the filter-processed color-component image and the filter-processed luminance-component image;

calculate an evaluation parameter based on the color-unevenness inspection image and the luminance-unevenness inspection image; and use the evaluation parameter to perform unevenness inspection in a manufacturing process of the inspection target independently from a capability of an inspector.

\* \* \* \* \*